(12) United States Patent
Zhao et al.

(10) Patent No.: US 10,772,482 B2
(45) Date of Patent: *Sep. 15, 2020

(54) EFFICIENT AND INTERACTIVE BLEEDING DETECTION IN A SURGICAL SYSTEM

(71) Applicant: Intuitive Surgical Operations, Inc., Sunnyvale, CA (US)

(72) Inventors: Wenyi Zhao, Mountain View, CA (US); Catherine J. Mohr, Mountain View, CA (US); Jonathan M. Sorger, Belmont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 293 days.

This patent is subject to a terminal disclaimer.

(21) Appl. No.: 15/863,651

(22) Filed: Jan. 5, 2018

(65) Prior Publication Data
US 2018/0125333 A1    May 10, 2018

Related U.S. Application Data

(63) Continuation of application No. 13/947,626, filed on Jul. 22, 2013, now Pat. No. 9,877,633.
(Continued)

(51) Int. Cl.
*A61B 1/00* (2006.01)
*A61B 5/02* (2006.01)
(Continued)

(52) U.S. Cl.
CPC ...... *A61B 1/00009* (2013.01); *A61B 1/00039* (2013.01); *A61B 1/00045* (2013.01);
(Continued)

(58) Field of Classification Search
CPC ... A61B 1/00009; A61B 1/00; A61B 1/00004; A61B 1/00039; A61B 1/00045;
(Continued)

(56) References Cited

U.S. PATENT DOCUMENTS

| 4,582,067 A | 4/1986 | Silverstein et al. |
|---|---|---|
| 5,170,792 A | 12/1992 | Sturgill et al. |

(Continued)

FOREIGN PATENT DOCUMENTS

| CN | 100558289 C | 11/2009 |
|---|---|---|
| CN | 102436638 A | 5/2012 |

(Continued)

OTHER PUBLICATIONS

Deschamps T., et al., "Vessel Segmentation and Blood Flow Simulation Using Level-Sets and Embedded Boundary Methods," International Congress Series, 2004, vol. 1268, pp. 75-80.
(Continued)

*Primary Examiner* — Matthew Kremer
*Assistant Examiner* — Avery M Foley

(57) ABSTRACT

A bleeding detection unit in a surgical system processes information in an acquired scene before that scene is presented on a display unit in the operating room. For example, the bleeding detection unit analyzes the pixel data in the acquired scene and determines whether there are one or more initial sites of blood in the scene. Upon detection of an initial site of blood, the region is identified by an initial site icon in the scene displayed on the display unit. In one aspect, the processing is done in real-time which means that there is no substantial delay in presenting the acquired scene to the surgeon.

20 Claims, 10 Drawing Sheets

Related U.S. Application Data

(60) Provisional application No. 61/675,484, filed on Jul. 25, 2012.

(51) Int. Cl.

| | | |
|---|---|---|
| *A61B 1/04* | (2006.01) | |
| *A61B 5/026* | (2006.01) | |
| *A61B 5/00* | (2006.01) | |
| *G06T 7/11* | (2017.01) | |
| *G06T 7/269* | (2017.01) | |
| *G06T 7/00* | (2017.01) | |
| *A61B 1/06* | (2006.01) | |
| *A61B 1/07* | (2006.01) | |
| *A61B 90/00* | (2016.01) | |
| *A61B 17/00* | (2006.01) | |
| *A61B 34/30* | (2016.01) | |

(52) U.S. Cl.
CPC ...... *A61B 1/00149* (2013.01); *A61B 1/00193* (2013.01); *A61B 1/04* (2013.01); *A61B 1/0661* (2013.01); *A61B 1/07* (2013.01); *A61B 5/0059* (2013.01); *A61B 5/02028* (2013.01); *A61B 5/02042* (2013.01); *A61B 5/0261* (2013.01); *A61B 5/742* (2013.01); *A61B 5/743* (2013.01); *A61B 90/37* (2016.02); *G06T 7/0016* (2013.01); *G06T 7/11* (2017.01); *G06T 7/269* (2017.01); *A61B 1/043* (2013.01); *A61B 34/30* (2016.02); *A61B 90/36* (2016.02); *A61B 2017/00119* (2013.01); *A61B 2090/3614* (2016.02); *G06T 2207/10024* (2013.01); *G06T 2207/30096* (2013.01)

(58) Field of Classification Search
CPC .............. A61B 1/00048; A61B 1/0005; A61B 1/00055; A61B 1/00149; A61B 1/00193; A61B 1/04; A61B 1/043; A61B 5/0059; A61B 5/02028; A61B 5/02007; A61B 5/02035; A61B 5/02042; A61B 5/0261; A61B 5/742; A61B 5/7425; A61B 5/743; A61B 34/30; A61B 90/36; A61B 90/361; A61B 2017/00119; A61B 2090/3614; A61B 1/0661; A61B 1/07; A61B 90/37; G06T 7/00; G06T 7/0012; G06T 7/10; G06T 7/11; G06T 7/12; G06T 7/13; G06T 7/269; G06T 7/0016; G06T 2207/10024; G06T 2207/30096

See application file for complete search history.

(56) References Cited

U.S. PATENT DOCUMENTS

| | | | |
|---|---|---|---|
| 9,877,633 B2 | 1/2018 | Zhao et al. | |
| 2002/0177779 A1 | 11/2002 | Adler et al. | |
| 2003/0018244 A1 | 1/2003 | Haddad et al. | |
| 2003/0213892 A1 | 11/2003 | Zhao et al. | |
| 2007/0066895 A1 | 3/2007 | Sikdar et al. | |
| 2007/0292011 A1 | 12/2007 | Nishimura et al. | |
| 2008/0108894 A1 | 5/2008 | Elgavish et al. | |
| 2009/0003675 A1 | 1/2009 | Moreau-Gobard | |
| 2009/0005691 A1 | 1/2009 | Huang et al. | |
| 2009/0196476 A1 | 8/2009 | Inoue | |
| 2010/0056936 A1 | 3/2010 | Fujii et al. | |
| 2010/0262017 A1 | 10/2010 | Frangioni | |
| 2012/0062717 A1 | 3/2012 | Kinouchi et al. | |
| 2014/0031659 A1 | 1/2014 | Zhao et al. | |

FOREIGN PATENT DOCUMENTS

| | | | |
|---|---|---|---|
| EP | 1672354 A1 | 6/2006 | |
| JP | 2006334115 A | 12/2006 | |
| JP | 2007330811 A | 12/2007 | |
| JP | 2008086605 A | 4/2008 | |
| JP | 2008093172 A | 4/2008 | |
| JP | 2011036372 A | 2/2011 | |
| JP | 2011200283 A | 10/2011 | |
| JP | 4861540 B2 | 1/2012 | |
| WO | WO-2008155861 A1 | 12/2008 | |
| WO | WO-2010138645 A2 | 12/2010 | |

OTHER PUBLICATIONS

Extended European Search Report for Application No. 13823451.3, dated Mar. 10, 2016, 7 pages.

International Search Report and Written Opinion for Application No. PCT/US13/51492, dated Oct. 24, 2013, 12 pages.

Ishihara R., et al., Infrared Endoscopic System for Bleeding-Point Detection after Flushing with Indocyanine Green Solution (with videos) [online], 2008 [retrieved on Jul. 20, 2011]. Retrieved from the Internet:< URL: http://www.ncbi.nlm.nih.gov/pubmed/18984104>.

Laparoscopy Hospital Safety during Electro Surgery, 2003, 27 pages [online] Retrieved from the internet: http://www.laparoscopyhospital.com/27658mdmasadundee.htm.

Lee Y.G., et al., "Bleeding Detection Algorithm for Capsule Endoscopy," International Journal of Medical, Health, Biomedical, Bioengineering and Pharmaceutical Engineering, 2011, vol. 5(9), pp. 388-393.

Liu J., et al., "Obscure Bleeding Detection in Endoscopy Images Using Support Vector Machines," Optim Engineering, 2008, vol. 10, pp. 289-299.

Milsom J.W., et al., "Advancing the Future of Minimally Invasive Surgery," 2009, 8 pages, [online]Retrieved from the Internet: http://www.olympusamerica.com/presspass/press_pass_cut/documents/generalsurgerynewsarticle_less.pdf.

Pan G., et al., "A Novel Algorithm for Color Similarity Measurement and the Application for Bleeding Detection in WCE," I.J. Image, Graphics and Signal Processing, 2011, vol. 5, pp. 1-7.

Penna B., et al., "A Technique for Blood Detection in Wireless Capsule Endoscopy Images," 17th European Signal Processing Conference (EUSIPCO 2009), 2009, pp. 1864-1868.

Reiter A., et al., "An Online Learning Approach to In-Vivo Tracking Using Synergistic Features," IEEE/RSJ International Conference on Intelligent Robots and Systems, Oct. 2010, pp. 3441-3446.

Scholz M., et al., "Virtual Image Navigation: A New Method to Control Intraoperative Bleeding in Neuroendoscopic Surgery," Journal of Neurosurgery, Aug. 2000, vol. 93(2), pp. 342-350.

Scott-Conner, D. Laparoscopic Prevention and Management of Active Hemorrhage, Principles of Laparoscopic Hemostasis, in: The SAGES Manual: Fundamentals of Laparoscopy, Thoracoscopy, and GI Endoscopy, 2006, pp. 67-68.

Van Pelt R., et al., "Exploration of 4D MRI Blood Flow Using Stylistic Visualization," IEEE Transactions on Visualization and Computer Graphics, 2010, vol. 16 (6), pp. 1339-1347.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

EFFICIENT AND INTERACTIVE BLEEDING DETECTION IN A SURGICAL SYSTEM

CROSS-REFERENCE TO RELATED APPLICATION

This application is continuation of U.S. patent application Ser. No. 13/947,626 (filed Jul. 22, 2013), which claims priority to and the benefit of U.S. Provisional Patent Application No. 61/675,484 (filed Jul. 25, 2012), each of which is incorporated herein by reference.

BACKGROUND

Field of Invention

Aspects of this invention are related to endoscopic imaging, and are more particularly related to detecting bleeding to provide a video display for a surgeon with real time bleeding motion.

Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery, and a shorter hospital stay. One key component of the da Vinci® Surgical System is a capability to provide two-channel (i.e., left and right) video capture and display of visible images to provide stereoscopic viewing for the surgeon.

Such electronic stereoscopic imaging systems may output high definition video images to the surgeon, and may allow features such as a "magnified" view that allows the surgeon to identify specific tissue types and characteristics, as well as to work with increased precision. In a typical surgical field when bleeding occurs, the predominant color becomes red, and the resulting blood may obscure the source of the bleeding itself, so bleeding and/or the location of bleeding may not be immediately apparent to the surgeon. In addition, the surgeon may be focused on critical tasks or a different specific region within the scene. Any one of these factors may result in a delay in observing and diagnosing the source of the bleeding.

SUMMARY

In one aspect, a scene of a surgical site is captured as a frame of pixel data by an image capture unit in a surgical system, such as robotic surgical system. A bleeding detection unit in the surgical system processes information in the frame of acquired pixel data before the scene is presented on a display unit in the operating room. For example, the bleeding detection unit analyzes the frame of pixel data and determines whether there are one or more new instances of blood in the scene. Upon detection of one or more new instances of blood, in one aspect, an initial site icon or icons is included in the scene displayed on the display unit. Each initial site icon identifies the position of a new instance of blood.

The pixel data acquired in each subsequent frame is analyzed by the bleeding detection unit. The region or regions of blood are identified and displayed on the display unit along with the initial site icon. Thus, a viewer sees an initial site icon and can watch the progression of the blood from the initial site. Even if the initial site becomes covered by a pool of blood, the initial site icon provides an indication of the bleeding site. Thus, the display of the initial site icon assists in locating the actual bleeding site.

In one aspect, the processing performed by the bleeding detection unit is done in real-time which means that there is no substantial delay in presenting the acquired scenes to the surgeon. Thus, the surgeon is made aware of bleeding by the initial site icon as soon as the blood is detected in the scene, and the surgeon can follow the progression of the bleeding over time.

The bleeding detection unit uses scenes normally acquired in, for example, a minimally invasive surgery by the image capture unit. The detection process does not require special cameras or other special equipment as in ultrasound or Doppler techniques.

More specifically, in one aspect, the bleeding detection unit in the surgical system receives an acquired frame of a surgical scene. The frame of pixel data includes a plurality of locations. Each location includes pixels for a plurality of color components.

The bleeding detection unit detects whether the plurality of color component pixels of each location includes information indicative of blood at that location. A region of blood in the scene is determined based on locations detected as including information indicative of blood.

If this is the initial detection of blood in the scene following a predetermined event, e.g., an initialization event or a suctioning event, the bleeding detection unit generates at least an initial site icon to indicate a position of the bleeding site in the scene. The initial site may also be indicated in some other way, e.g., by highlighting the initial site in the scene. If this was not the initial detection of blood in the scene, optionally the region of blood in the scene is indicated using a blood marker that is different from the initial site icon, e.g., a different icon, a different false coloring, a different border, etc.

The initial site icon and the optional blood marker are combined with the surgical scene to obtain a combined image. The combined image is then displayed on a display unit in the operating room, in one aspect. Thus, initially the initial site icon is presented and then over time, the initial site icon remains in the scene while the progression of the bleeding is indicated by the blood marker. In some aspects, the blood marker is not used and only the initial site icon is used. The combination of the initial site icon and the display of the progression of the bleeding over time assists the surgeon and/or other personal in the operating room in determining the location of the bleeding site.

In one aspect, the determination of whether the plurality of color component pixels of each location includes information indicative of blood at that location includes generating a ratio in which a first quantity in the ratio contains a first color component pixel value at the location and in which a second quantity in the ratio includes a second color component value at the location. The location is identified as including information indicative of blood if the ratio has a predefined relationship to a blood indication threshold, e.g., the ratio is larger than the blood indication threshold.

In another aspect, the bleeding detection unit estimates the blood flow in a region of blood. Indicators of the blood flow are combined with the acquired scene and displayed on the display unit along with any blood marker and the initial site icon.

In this aspect, the bleeding detection unit estimates a gross motion of each location in the region using an optical flow analysis on a plurality of frames. An estimate of the blood flow at the location is generated by correcting the estimated gross motion of the location to compensate for average tissue motion at the location. A simulated flow of blood in the scene is generated from the blood flows of the plurality of locations.

In another aspect, an interactive method includes receiving an automatically generated warning of bleeding on a display unit during a surgical procedure. Following the warning, a physical area corresponding to a region of blood presented on the display unit is cleaned by manipulation of a surgical instrument. Next, a location of the localized bleeding source is determined from information presented on the display unit. The bleeding source is treated to attenuate the bleeding by manipulation of a surgical instrument mounted in the minimally invasive surgical system. Finally, it is determined whether the treating process attenuated the bleeding by using information presented on the display unit.

A system includes an image capture system configured to acquire a frame of data of a surgical scene. The frame of data includes a plurality of locations. Each location includes pixels for a plurality of color components. A bleeding detection unit, in the system includes a region segmentation module and a region of blood identification module. The system also includes a display unit coupled to the bleeding detection unit to receive a combined scene and configured to display the combined scene.

The region segmentation module is configured to receive the frame of data; to detect whether the plurality of color component pixels of each location includes information indicative of blood at that location; and to determine a region of blood in the scene based on locations detected as including information indicative of blood.

The region of blood identification module is coupled to the region segmentation module. The region of blood identification module is configured to generate an initial site icon to indicate the region of blood in the scene, and to combine the initial site icon with the scene to generate the combined scene.

The bleeding detection unit also includes a blood flow estimator module. The blood flow estimator module generates the flow of blood in the region of blood relative to any motion of the region. The blood flow estimator module includes an estimate motion module that estimates gross motion at each location in the region. The blood flow estimator module also includes a correction motion module coupled to the estimate motion module. The correction motion module corrects the gross motion at each location in the region to generate the flow of blood at each location relative to the motion of the region.

Figure 1:
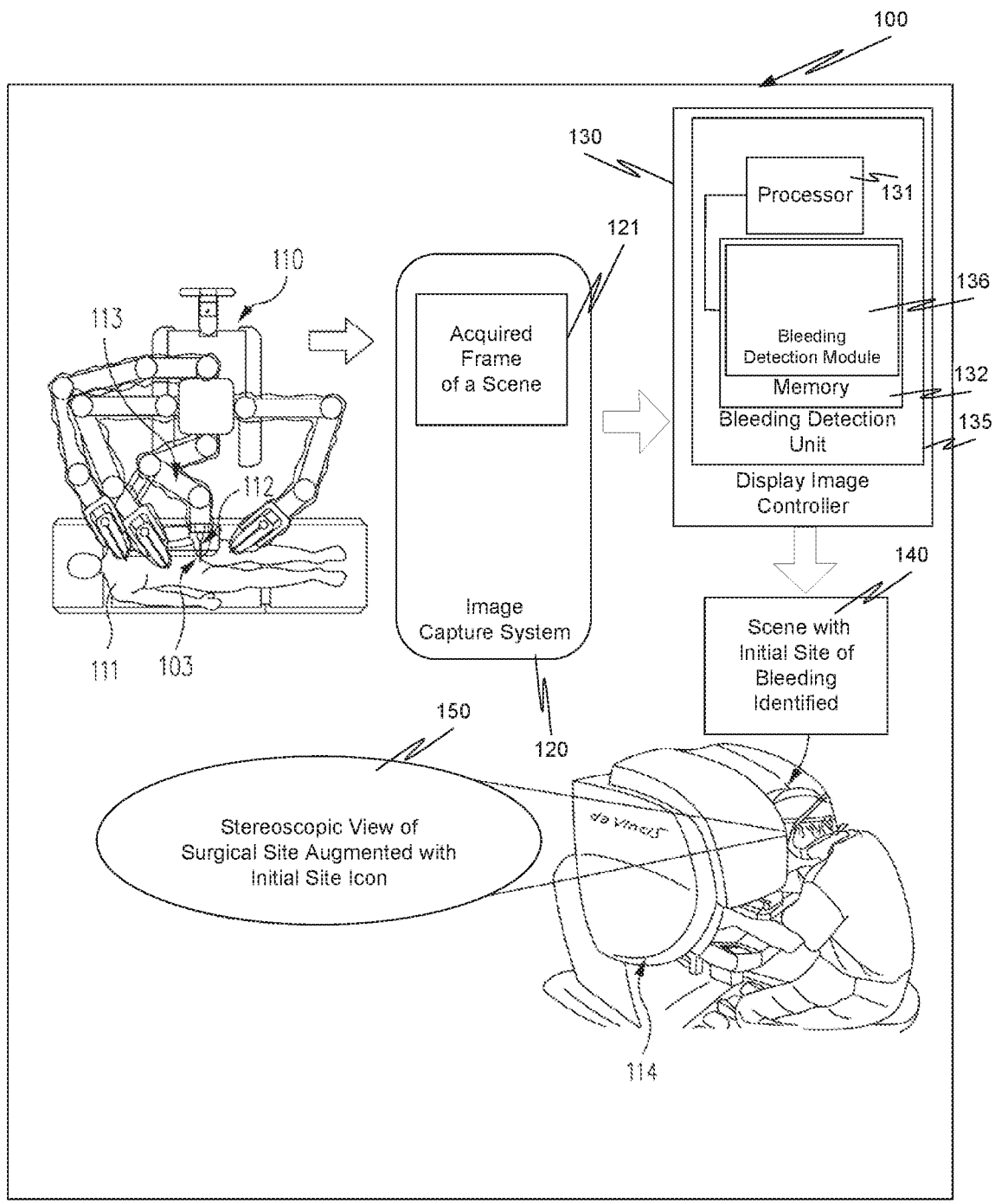
FIG. 1 is a high-level diagrammatic view of a surgical system including a bleeding detection unit.

In the drawings, the first digit of a reference number indicates the figure in which the element with that reference number first appeared.

DETAILED DESCRIPTION

FIG. 1 is a high-level diagrammatic view of a surgical system 100, for example, the da Vinci® Surgical System, including a bleeding detection unit 135. (da Vinci® is a registered trademark of Intuitive Surgical, Inc. of Sunnyvale, Calif.) In this example, a surgeon, using master controls at a surgeon's console 114, remotely manipulates an endoscope 112 mounted on a robotic manipulator arm 113 that in turn is mounted on cart 110. The surgeon also remotely manipulates one or more surgical instruments coupled to cart 110. There are other parts, cables, etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 23, 2007; disclosing Minimally Invasive Surgical System), U.S. Pat. No. 6,837,883 B2 (filed Oct. 5, 2001; disclosing Arm Cart for Telerobotic Surgical System), and U.S. Pat. No. 6,331,181 (filed Dec. 28, 2001; disclosing Surgical Robotic Tools, Data Architecture, and Use), all of which are incorporated herein by reference. The use of a teleoperated minimally invasive surgical system is illustrative only and is not intended to limit the invention to this specific system. In view of this disclosure, the aspects described herein can be incorporated in a robotic surgical system or other surgical system that includes the elements necessary to implement the aspects described herein.

Endoscope 112 includes, in one aspect, two optical channels for passing light from the tissue, e.g., reflected light and/or fluorescence. The light reflected from tissue 103 of patient 111 in each of the optical channels is captured as a scene so that at each point in time, two scenes are captured, a left scene and a right scene. Each captured scene is contained in a frame of data 121. Two frames of data, a left frame and right frame, are captured by image capture system 120 at a particular point in time. The two frames of data are processed and the resulting scenes are presented on a stereoscopic display unit in surgeon's control console 114, sometimes referred to as surgeon's console 114 or simply console 114.

The use of a stereoscopic endoscope and a stereoscopic display are illustrative only and are not intended to be limiting. The aspects described herein can be applied to systems that do not include the stereoscopic features such as monoscopic endoscopes and/or normal display units.

In one aspect, following a predetermined event, e.g., a surgeon enabling bleeding detection unit 135, an initialization event of bleeding detection unit 135, a suction event (See FIG. 3B), etc., bleeding detection unit 135 processes information in an acquired scene before that scene is presented as part of a stereoscopic scene on surgeon's console 114. For example, bleeding detection unit 135 analyzes the pixel data in the left and right acquired frames and determines whether there are one or more initial instances of blood in the acquired scenes. Upon detection of such an initial instance, bleeding detection unit 135 generates a pair of scenes 140 (a left scene and a right scene) in which an initial site of the blood is identified by an initial site icon, and sends the pair of scenes 140 to a stereoscopic display system in surgeon's console 114. A stereoscopic scene 150 with the initial site icon is displayed on surgeon's console 114.

In one aspect, the processing of the left and right acquired frames is done in real-time, which means that there is no substantial delay in presenting the acquired scenes to the surgeon. The surgeon is made aware of the bleeding as soon as the initial instance of blood is detected in the scenes. Thus, each frame in a sequence of frames is processed and the scenes in those frames are presented to the surgeon on the display at essentially the same time as the bleeding is occurring at the surgical site. This means that the surgeon does not see the bleeding in the displayed scene and then subsequently sees a bleeding indication in the displayed scene. In this aspect, the two events occur at the same time as viewed by the surgeon. In this aspect, the bleeding detection capability does not require delaying the presentation of a frame until after the capture of a subsequent frame.

For example, to raise the surgeon's awareness of the bleeding, in one aspect, a flashing arrow or some other icon points to the initial site on the display unit in surgeon's console 114. In addition, or alternatively, the icon may be or may include a boundary drawn around the initial site, or the initial site may be false colored so that the surgeon can easily visualize the position where blood was first detected. In some aspects, in addition to the visual warning, an auditory warning may be generated. These examples are illustrative only of some of the possible means of notification and are not intended to be limiting to these specific ways to notify the surgeon and/or other personal involved in the surgical operation.

After detection of an initial site of blood in a frame, the pixel data acquired in each subsequent frame is analyzed by bleeding detection unit 135 and the site or sites of blood in that frame may be identified in the scene displayed on console 114 for that frame along with the initial site icon. For example, a blood marker is used to indicate the region of blood. The blood marker, for example, is highlighting the region in some way, e.g., a border, false coloring, etc. If an instance of blood is detected in a subsequent frame that is not part of the blood surrounding an initial site icon, an initial site icon is associated with that instance of blood, in one aspect.

Thus, a viewer sees on the display unit at least an initial site icon and can watch as the blood increases from the initial site. While in one aspect, the processing done for each set of frames is static—is blood present or not—as the amount of blood in the scene increases due to the bleeding, the time sequential presentation of the acquired scenes provides information on the flow and amount of the bleeding. In addition, even if the initial site becomes covered by a pool of blood, the initial site icon provides an indication of the initial position where blood was detected. Thus, the initial site icon assists in locating the actual site that is bleeding. For example, the surgeon can reach with bipolar graspers into the pool of blood, find the place where it is bleeding (even if the surgeon cannot see the place), and stop the bleeding.

The assistance of the initial site icon is used for both two-dimensional images from a monoscopic endoscopic and for three-dimensional images from a stereoscopic endoscope. As is known to those knowledgeable in the field, a three-dimensional image is perceived by the surgeon when the left and right scenes are presented on the stereoscopic display unit. When an initial site icon is presented in the left and right displayed scenes, the resulting three-dimensional image provides the surgeon with better guidance on how to move the graspers to the bleeding site than the two dimensional image does.

While identifying the initial site where blood was detected quickly alerts the surgeon to bleeding, in some aspects, an estimated flow of the blood relative to motion in the scene is also presented in the visual display of the image. The estimated blood flow further assists the surgeon in locating the bleeding site by providing information that also localizes the site of bleeding.

Hence, bleeding detection unit 135 automatically detects and localizes bleeding sites based on reliable blood detection and motion estimation. In one aspect, the automatic detection is continuously applied to warn the person viewing the display of bleeding during a surgical procedure. Applying motion detection to a detected region of blood not only saves time in locating the bleeding site, but also makes the detection process more robust. The detection and localization of bleeding is done without detecting or monitoring the motion of surgical instruments. As explained more completely below, bleeding detection unit 135 provides robust detection of blood and of the blood motion from the bleeding site even in the presence of breathing or other tissue motion.

Figure 2:
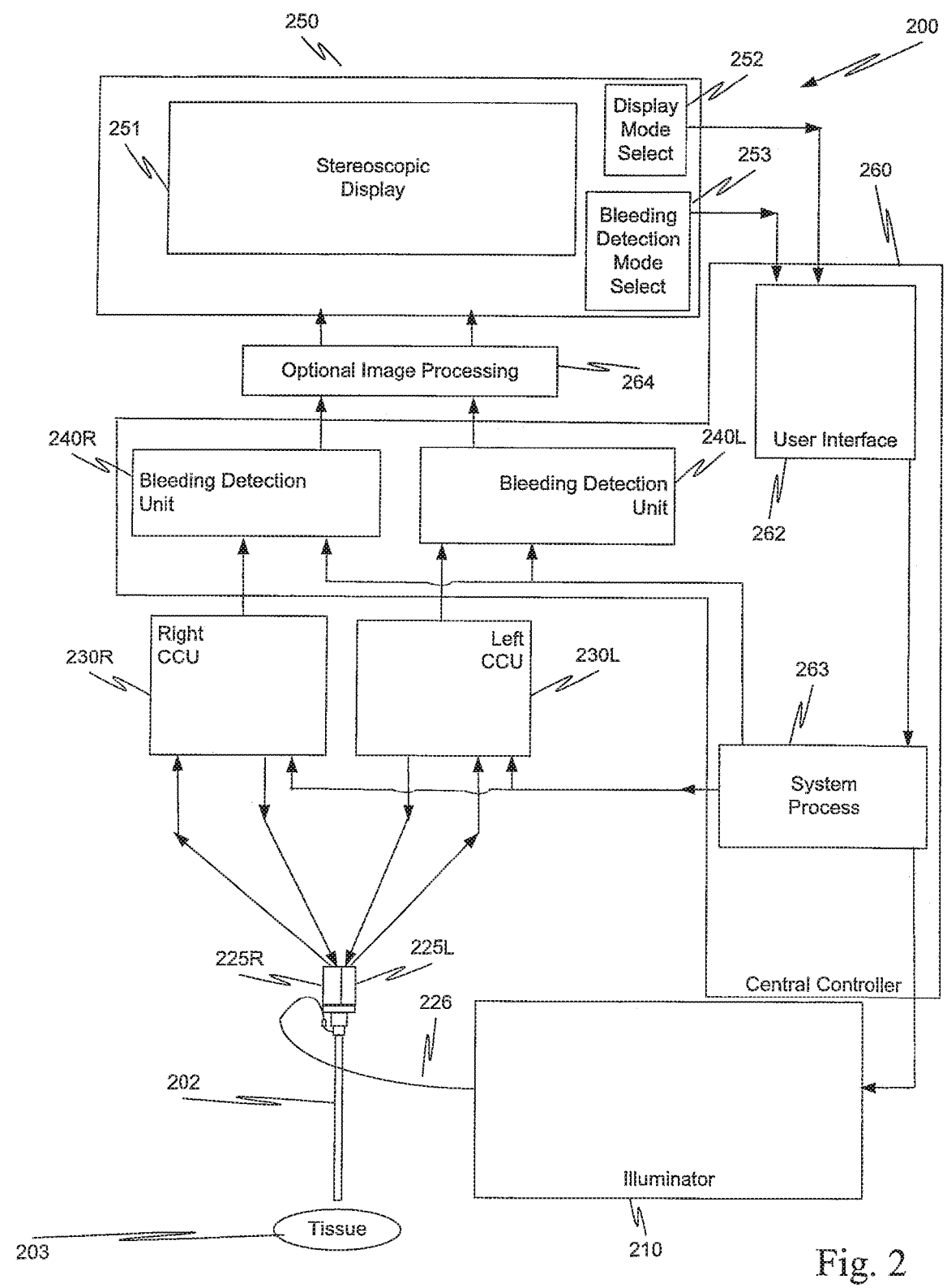
FIG. 2 is a schematic view that illustrates hardware and software aspects of the surgical system including the bleeding detection unit.
Figure 3A:
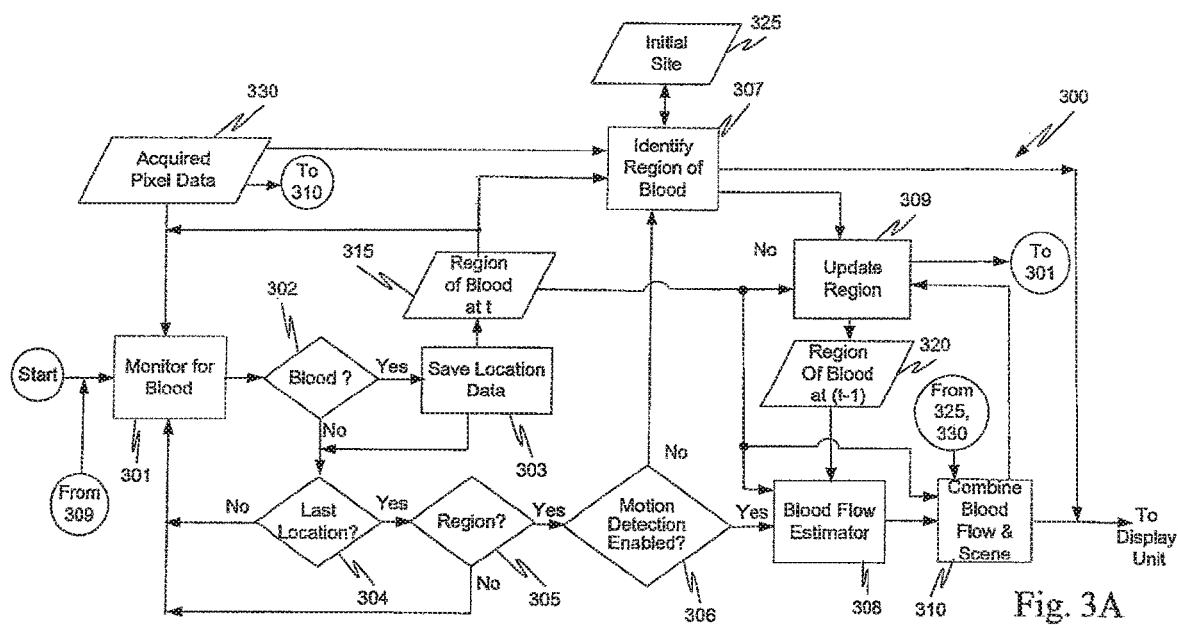
FIG. 3A is a process flow diagram of processes performed by the bleeding detection units of FIGS. 1 and 2.
Figure 3B:
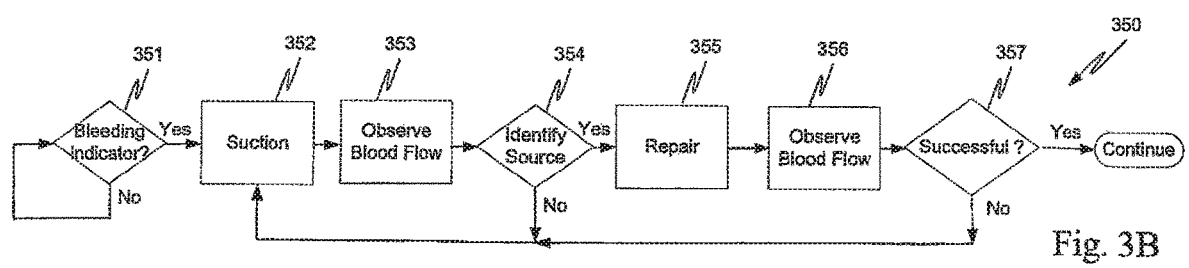
FIG. 3B is a process flow diagram of an interactive method that uses the information provided by the bleeding detection units.

FIG. 2 is a more detailed illustration of the aspects of one example of surgical system 100 of FIG. 1. FIG. 3A is a process flow diagram representing aspects of the operation of bleeding detection units 240R, 240L. Bleeding detection units 240R, 240L are an example of one implementation of bleeding detection unit 135. FIG. 3B is a process flow diagram representing an aspect of the use of the information provided by bleeding detection units 240L, 240R. FIGS. 4A to 4F are examples of scenes based on the processes of FIGS. 3A and 3B. While in FIG. 2, bleeding detection units 240R, 240L are shown as two separate units, in some aspect, the two units are combined in a single bleeding detection unit. Also, in some aspects, as described more completely below, bleeding detection units 240R, 240L do not function completely independently.

In the embodiment of minimally invasive surgical system 200 illustrated in FIG. 2, an illuminator 210 is coupled to stereoscopic endoscope 202. Illuminator 210 includes at least a white light source and optionally may include one or more fluorescence excitation sources, for example near infrared illumination. Illuminator 210 is used in conjunction with at least one illumination channel in stereoscopic endoscope 202 to illuminate tissue 203. Alternatively and without loss of generality, illuminator 210 may be replaced by an illumination source at the distal tip, or near the distal tip, of endoscope 202. Such distal tip illumination may be provided by light emitting diodes (LEDs), for example, or other illumination sources.

In one example, illuminator 210 provides white light illumination that illuminates tissue 203. In some implementations, illuminator 210 can also provide other types of illumination, e.g., non-visible light that excites fluorescence and as well as a subset of the visible color components that make-up white light.

Light from illuminator 210 is directed onto an illumination channel 226 that couples illuminator 210 to the illumination channel in endoscope 202. The illumination channel in stereoscopic endoscope 202 directs the light to tissue 203.

The illumination channels can be implemented, for example, with a fiber optic bundle, a single stiff or flexible rod, or an optical fiber.

In one aspect, each of image capture units 225R, 225L captures light reflected from tissue 203, i.e., captures a frame of data. The frame of data represents a surgical scene. The image capture sensors in image capture units 225R, 225L can be multiple CCDs that each capture a different visible color component; a single CCD with different regions of the CCD that capture a particular visible color component, etc; a three-chip CCD sensor, a single CMOS image sensor with a color filter array, or a three-CMOS color image sensor assembly, for example.

Image capture unit 225L is coupled to a stereoscopic display unit 251 in surgeon's console 250 via a left camera control unit (CCU) 230L. Image capture unit 225R is coupled to stereoscopic display unit 251 in surgeon's console 250 via a right camera control unit (CCU) 230R. Camera control units 230L, 230R receive signals from a system process module 263 that controls gains, controls capturing images, controls transferring frames of data to bleeding detection units 240R, 240L, etc. System process module 263 represents the various controllers including the vision system controllers in system 200. Camera control units 230L, 230R may be separate units, or may be combined in a single dual controller unit.

Display mode select switch 252 provides a signal to a user interface 262 that in turn passes the selected display mode to system process module 263. Various vision system controllers within system process module 263 configure illuminator 210 to produce the desired illumination, configure left and right camera control units 230L and 230R to acquire the desired data, and configure any other elements needed to process the acquired frames so that the surgeon is presented the requested images in stereoscopic display unit 251. While in this aspect, the scenes displayed on a surgeon's console are discussed, the scenes can also be displayed on other monitors located in the operating room or elsewhere.

As shown in FIG. 2, user interface 262, system process module 263, and bleeding detection units 240L, 240R are grouped as a central controller 260 for descriptive purposes. Central controller 260 also typically includes color correction modules that transform the color of the scenes to a new desired color balance as determined by system process module 263. Optional image processing module 264 receives video from central controller 260 and processes scenes from color correction modules prior to display on stereoscopic display unit 251 in surgeon's console 250.

The color correction modules and optional image processing module 264 are equivalent to image processing modules in prior art minimally invasive surgical systems and so are not considered in further detail.

Each of bleeding detection units 240R, 240L function the same and so only one of the units, bleeding detection unit 240R, is considered in detail. The description is directly applicable to the other unit, bleeding detection unit 240L, and so in not repeated. However, as explained more completely below, the stereoscopic constraints on the scenes captured in the left and right channels of system 200 are used to help eliminate false blood detection.

Also, processing associated with a single acquired frame is described. However, this processing is applied to each acquired frame or some subset of the acquired frames so that a continuous stream of scenes are provided to stereoscopic display unit 251 in surgeon's console 250. In addition, it should be understood that when blood flow estimation is performed, data of frames at two different points in time, e.g., time (t−1) and time t, are used even though the blood flow estimation is discussed with respect to the frame at time t. Also, stereoscopic processing equivalent to the prior art stereoscopic processing is done with respect to the scenes processed and produced by bleeding detection units 240R, 240L. Since the stereoscopic processing is known, it is not considered in further detail except when applicable to bleeding detection.

In one aspect, bleeding detection unit 240R performs process 300 (FIG. 3A) by executing a bleeding detection module 136 on a processor 131. In this aspect, bleeding detection module 136 is stored in a memory 132. However, this is illustrative only and is not intended to be limiting. Bleeding detection module 136 can be implemented in hardware, in firmware, in executing software, or any combination of the three.

In a MONITOR FOR BLOOD process 301, pixel data 330 in an acquired frame is processed. An acquired frame of pixel data includes a plurality of (i, j) locations. For example, a frame may have 1920 horizontal locations (i) and 1080 vertical locations (j).

Typically, each location (i, j) in the frame has a set of pixels, where the value of a pixel is a value of a color component in a color space. For a typical red-green-blue component color space, there is a red pixel, a green pixel, and blue pixel for each location (i, j). Herein, each location (i, j) in an acquired frame of pixel data is defined as having pixel data for a plurality of color components. An alternative definition is that there is a color pixel (i, j) that includes a plurality of color components at location (i, j).

For a location (i, j), MONITOR FOR BLOOD process 301 analyzes pixel data for a group of locations including location (i, j) to determine a blood measurement BM for location (i, j). For example, MONITOR FOR BLOOD process 301 can use a texture detection process to characterize a location as being indicative of a location in a texture pattern or not being indicative of a location in a texture pattern. Blood has a smooth variation of color over a region, while a texture pattern has a statistical variation of color over a region. Certain organs have a definite texture pattern, e.g., a known statistical variation of color over a region that can be used in process 301. For example, the color variation for the liver is large and varies between red and white, while the color variation for blood is confined to smaller variations in red.

Alternatively, in MONITOR FOR BLOOD process 301, or in addition to the texture processing, a ratio can be formed using a set of the color components for location (i, j) and a value of the ratio is blood measurement BM(i, j). After blood measurement BM(i, j) is generated for location (i, j), MONITOR FOR BLOOD process 301 transfers to BLOOD check process 302.

BLOOD check process 302 compares blood measurement BM(i, j) to a known standard to determine whether blood measurement BM(i, j) is indicative of blood at location (i, j). For example, if a texture detection process was used in MONITOR FOR BLOOD process 301, BLOOD check process 302 determines whether the blood measurement is indicative of a tissue texture pattern or indicative of blood. If the blood measurement is indicative of a tissue texture pattern, blood is not considered to be at location (i, j) and BLOOD check process 302 transfers to LAST LOCATION check process 304. Conversely, if the blood measurement is indicative of blood at location (i, j), BLOOD check process 302 transfers to SAVE LOCATION DATA process 303.

In one aspect, SAVE LOCATION DATA process 303 saves the pixel data for location (i, j) in REGION OF BLOOD AT TIME t data 315 and then transfers to LAST LOCATION check process 304. Process 303 should not be interpreted as requiring saving the pixel data for location (i, j) in a buffer. Any desired technique can be used to identify location (i, j) as indicative of blood. For example, a bit or bits could be configured in ACQUIRED PIXEL DATA 330 to indicate that location (i, j) is indicative of blood. A bit mask could also be created that selects the locations in ACQUIRED PIXEL DATA 330 that are indicative of blood. Thus, SAVE LOCATION DATA process 303 saves information that identifies location (i, j) in the frame of pixel data as being indicative of blood.

Similarly, if blood measurement BM(i, j) is a ratio and texture processing is not used, BLOOD check process 302 compares the value of blood measurement BM(i, j) with a blood indication threshold. In one aspect, if blood measurement BM(i, j) is larger than the blood indication threshold, blood is considered to be present at location (i, j). Conversely, if blood measurement BM(i, j) is smaller than the blood indication threshold, blood is not considered to be present at location (i, j).

If blood measurement BM(i, j) is indicative of blood, BLOOD check process 302 transfers to SAVE LOCATION DATA process 303. In this aspect, SAVE LOCATION DATA process 303 saves the pixel data in the acquired frame at location (i, j) in REGION OF BLOOD AT TIME t data 315 and then transfers to LAST LOCATION check process 304. If blood is not considered to be at location (i, j), check process 302 transfers to LAST LOCATION check process 304.

In another aspect, BLOOD check process 302 uses the combination of the texture pattern checking and the ratio checking. If the texture pattern checking is indicative of blood, the ratio checking is performed for location (i, j) to determine whether to save the pixel data at location (i, j) in data 315. In this aspect, the pixel data at location (i, j) is saved in data 315 only when both the texture pattern checking and the ratio checking are indicative of blood at location (i, j).

In still yet another aspect, the stereoscopic relationship between the scenes captured in the left and right channels is used to help detect false positive indications of blood in BLOOD check process 302. However, the distance from the image capture sensor to location (i, j) is not known. To check for blood at location (i, j) in both the left and right channels requires matching the scenes in the left and right channel. One technique for performing the matching automatically is described in U.S. Patent Publication No. US 2010/0166323 A1 (disclosing "Robust Sparse Image Matching for Robotic Surgery"), which is incorporated herein by reference. With this matching if blood is detected at a location in one of the left and right scenes and not at the corresponding location in the other of the left and right scenes, the blood detection is considered a false positive and so BLOOD check process 302 does not find blood at location (i, j).

LAST LOCATION check process 304 determines whether all the locations of interest in ACQUIRED PIXEL DATA 330 have been processed by MONITOR FOR BLOOD process 301. If all the locations have been processed, check process 304 transfers to REGION check process 305 and otherwise to MONITOR FOR BLOOD process 301.

In some aspects, not all the locations in a frame are checked to determine whether blood is present. For example, when the perimeter region in a captured scene is quite dark, the pixel data for locations in the perimeter may not convey sufficient information to facilitate detection of blood. Accordingly, the pixel data at each location in ACQUIRED PIXEL DATA 330 may be filtered, and locations having a luminance less than a perimeter threshold value are not processed for the presence of blood.

Similarly, reflected light from surgical instruments may saturate pixel data in ACQUIRED PIXEL DATA 330. Locations that have saturated pixel data do not convey any meaningful information with respect to blood detection and so are not processed in one aspect. In one aspect, to minimize the effects of specular reflections, the light reflected from tissue 203 is passed through a polarizer that blocks such reflected light so that specular reflection effects are diminished in the acquired data.

In some clinical settings, selected locations in the frame may not be of interest with respect to detecting blood, e.g., in a region that is within the fovea of the surgeon, in a region where tissue is being cut, or in a region for which the surgeon has turned off blood detection. As explained more completely below, such regions can be exempted from blood detection. Nevertheless, the automatic blood and bleeding detection processes described herein are powerful tools for detecting blood in regions outside the surgeon's small foveae and in regions that have not been exempted from blood detection due to darkness, saturation, or other criteria.

When all the locations of interest in ACQUIRED PIXEL DATA 330 have been processed by processes 301, 302, 303, and 304, data 315 contains pixel data for a region or regions in ACQUIRED PIXEL DATA 330 that is indicative of blood. If no region of blood is detected, data 315 remains at the initialized state. Thus, it has been determined whether there is a region or regions of blood in the acquired scene.

REGION check process 305 determines whether there is a least one region of blood in data 315. If there is at least one region of blood in data 315, REGION check process 305 transfers to MOTION DETECTION ENABLED check process 306, and otherwise returns to MONITOR FOR BLOOD process 301.

In one aspect during the initialization of method 300, several flags are initialized. For example, an initial site flag is set to a predetermined state, e.g., true, a display blood region flag is set to a default state, e.g., a display blood region disabled state, and a motion estimation flag is set to a default state, e.g., a motion detection disabled. In one aspect, a user can specify the state of one or more of these flags through a user interface such as user interface 262. The use of flags is illustrative only and is not intended to be limiting. In view of this disclosure, the aspects described can be implemented in a variety of ways to accomplish the results associated with each aspect.

MOTION DETECTION ENABLED check process 306 determines the state of the motion estimation flag, i.e., is motion detection enabled. To do an estimation of the motion of the blood, two frames of pixel data are required-one frame at time t and one frame at time (t−1). For the first frame, a second frame of data is not available and so data for a motion estimation for time t is not available. Even when a second frame of data is available, motion estimation may not be wanted until after a known point in time, e.g., after the region of blood is suctioned or irrigated. Thus, the motion estimation flag remains in a first state, disabled, until the suction is completed and then the motion estimation flag is set to a second state, e.g., enabled.

The state of the motion estimation flag can be used in two ways. In a first aspect, blood flow estimator module 708 (FIG. 7) is not run until the motion estimation flag has the second state. In a second aspect, blood flow estimator module 708 (FIG. 7) is started upon initialization of the system, for example, and is running in the background so that when the motion estimation flag changes to the second state, blood flow estimates are ready and available for use. In the second aspect, the motion estimation flag is used to control the information that is sent to the display unit, e.g., either include the motion estimation data or do not include the motion estimation data.

When the motion estimation flag has the first state, MOTION DETECTION ENABLED check process 306 transfers to IDENTIFY REGION OF BLOOD process 307. IDENTIFY REGION OF BLOOD process 307, in one aspect, first determines whether the initial site flag has the first state, true. If initial site flag has the first state, it means that the frame of acquired pixel data is a first frame after a site initialization event, e.g., a bleeding detection unit initialization event, a suction event, an irrigation event, or another event defined by a user. Thus, in one aspect, IDENTIFY REGION OF BLOOD process 307 saves information characterizing the site in INITIAL SITE data 325 when the initial site flag is true and then sets the initial site flag to a second state, e.g., false. Other techniques may be used in IDENTIFY REGION OF BLOOD process 307 to detect initial instances of blood in a frame, e.g., a site of blood that is not connected to any other sites of blood in the frame.

IDENTIFY REGION OF BLOOD process 307 uses the information in INITIAL SITE data 325 to determine where to place an initial site icon in the surgical scene. IDENTIFY REGION OF BLOOD process 307 combines the initial site icon with the acquired pixel data and sends the combined information to display unit 251 via optional image processing module 264. Process 307 identifies each different site of blood in the initial frame of acquired pixel data. Process 307 includes the initial site icon in each subsequent frame of data that is sent to the display unit until another site initialization event occurs.

In one aspect, the initial site icon is an arrow that points to a region of blood in the scene displayed on stereoscopic display unit 251. In addition, or alternatively, the initial site icon may include a boundary drawn around the initial region of blood, or each initial region may be false colored so that the surgeon's can easily identify the position in the scene where blood was initially detected. In some aspects, in addition to the visual warning, an auditory warning is generated by process 307. Again, these examples are illustrative only of some of the possible means of notification and some of the possible site icons. These examples are not intended to be limiting, but rather illustrative of ways to notify the surgeon and/or other personal involved in the operation of the detection of bleeding.

IDENTIFY REGION OF BLOOD process 307 also transfers to UPDATE REGION process 309. In one aspect, UPDATE REGION process 309 changes a current region pointer that addresses REGION OF BLOOD AT TIME t data 315 to a previous region pointer so that REGION OF BLOOD AT TIME t data 315 becomes REGION OF BLOOD AT TIME (t−1) data 320. After UPDATE REGION process 309 saves REGION OF BLOOD AT TIME t data 315 as REGION OF BLOOD AT TIME (t−1) data 320; UPDATE REGION process 309 returns to MONITOR FOR BLOOD process 301.

The particular method used by UPDATE REGION process 309 to save the data in REGION OF BLOOD AT TIME t data 315 as data in REGION OF BLOOD AT TIME (t−1) data 320 is not critical. The method selected is determined, for example, by the memory available, processing capability, etc.

Figure 4A:
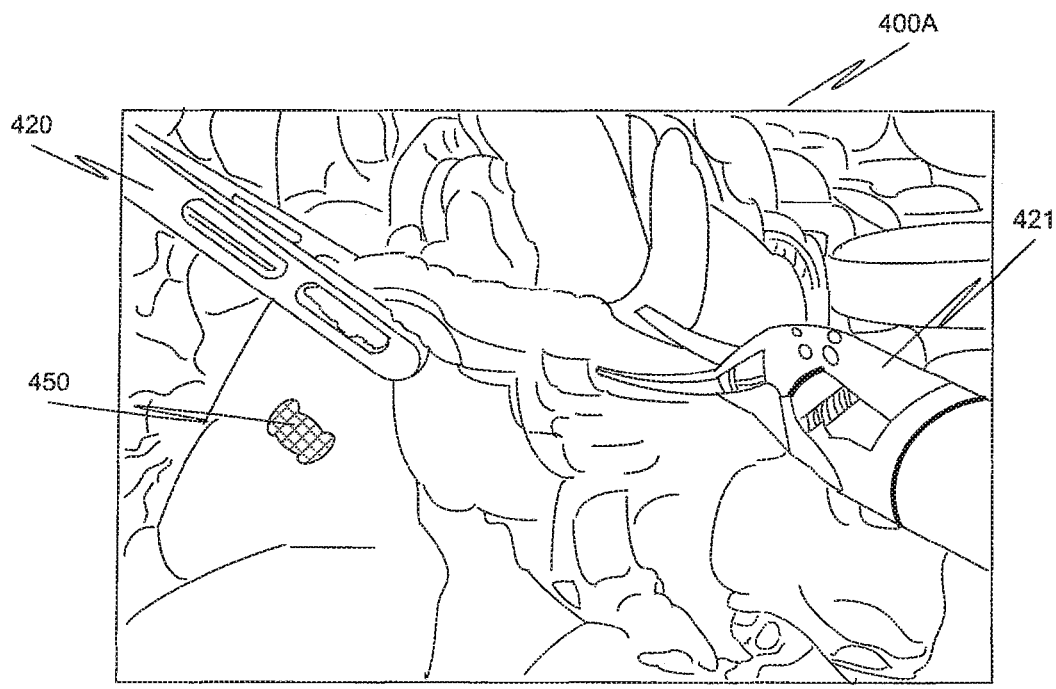
FIGS. 4A to 4F are examples of scenes based on the processes of FIGS. 3A and 3B.

FIG. 4A is a surgical scene 400A that is displayed on stereoscopic display unit 251. Scene 400A includes two teleoperated minimally invasive surgical instruments 420, 421. There is bleeding in scene 400A, which is represented by crosshatched region 450. In the prior art, the surgeon or an assistant would have to notice and identify crosshatched region 450 as blood. However, if the surgeon's focus was on a region near one of the surgical instruments, it may take some time for the surgeon to notice the bleeding at which time the origin of the bleeding may be obscured by the blood.

Figure 4B:

However, with bleeding detection unit 135, when the acquired pixel data for scene 400A is processed by processes 301, 302, 303, 304, 306, and 307, blood is detected. Thus, process 307 superimposes an initial site icon 460B, e.g., arrow 460B (FIG. 4B), on region of blood 451 in scene 400B. Also, in this example, region of blood 451 was false colored, e.g., displayed as green, to make initial region of blood 451 stand out from the rest of the displayed scene. In FIG. 4B, stippling is used to represent the false coloring. Arrow 460B and the false coloring of region 451 would be detected at least in the peripheral vision of the surgeon and so the bleeding would be detected much sooner relative to scene 400A.

Returning to method 300 (FIG. 3A), UPDATE REGION process 309 transferred to MONITOR FOR BLOOD process 301 to start processing the next frame of acquired pixel data. When processes 301, 302, 303, 304 complete the processing of the next frame of acquired pixel data, the region or regions of blood are available in REGION OF BLOOD AT TIME t data 315.

Figure 4C:
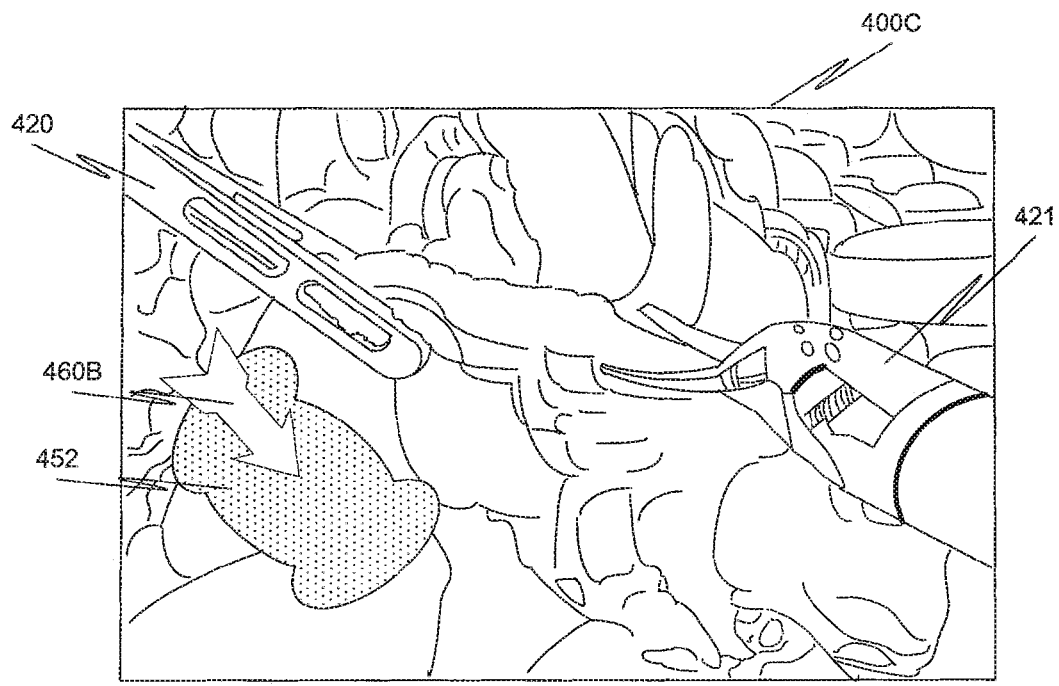
Figure 4D:
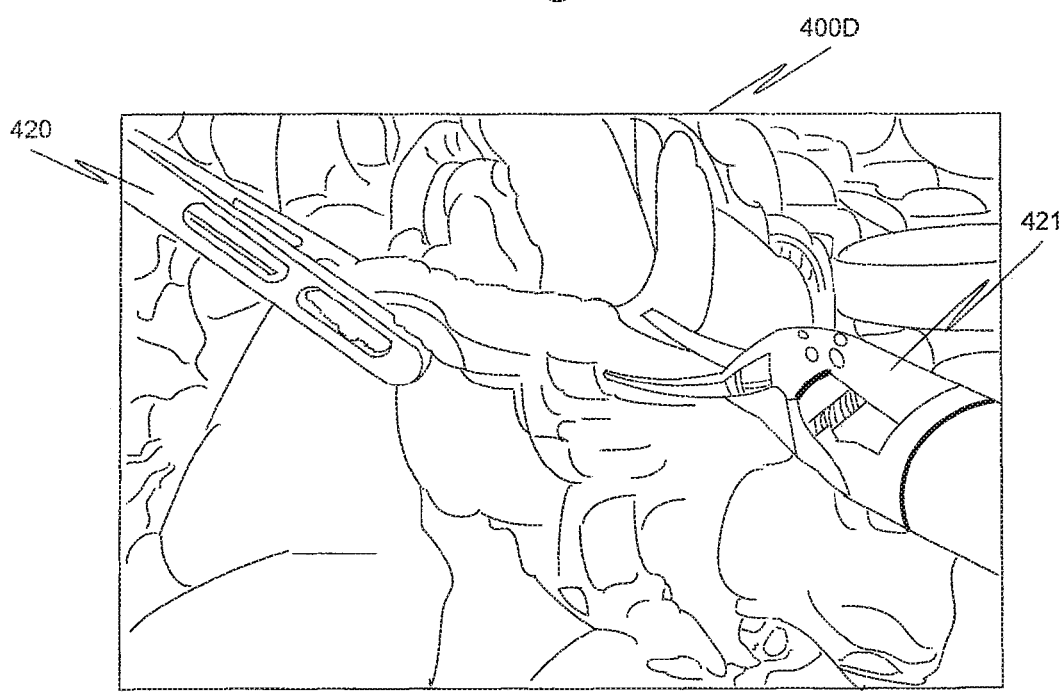
Figure 4E:
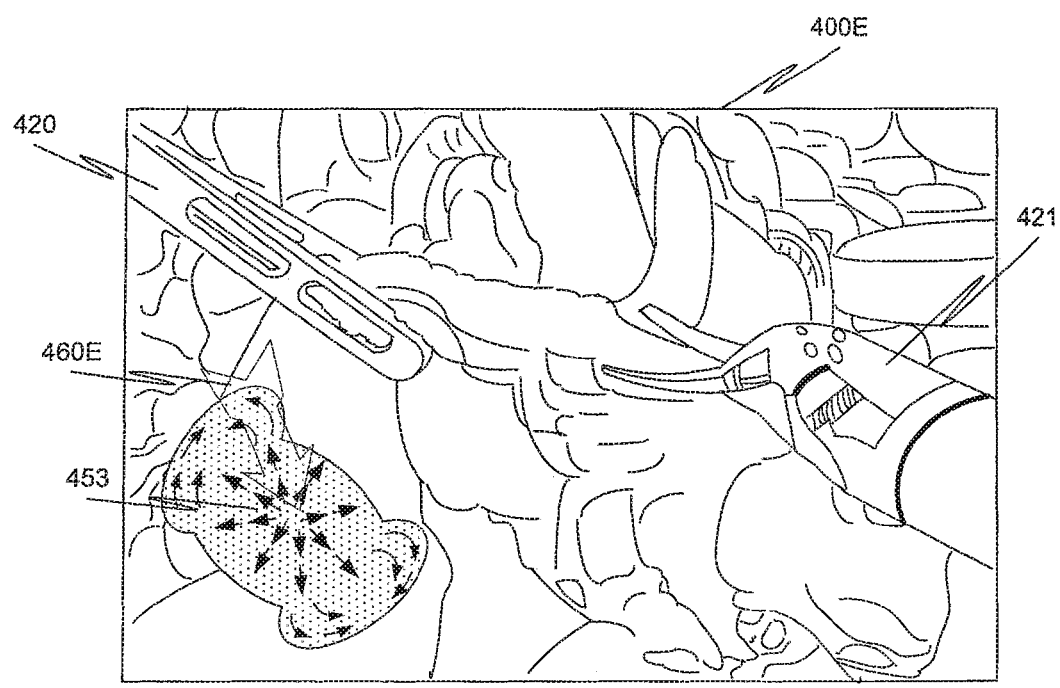
Figure 4F:
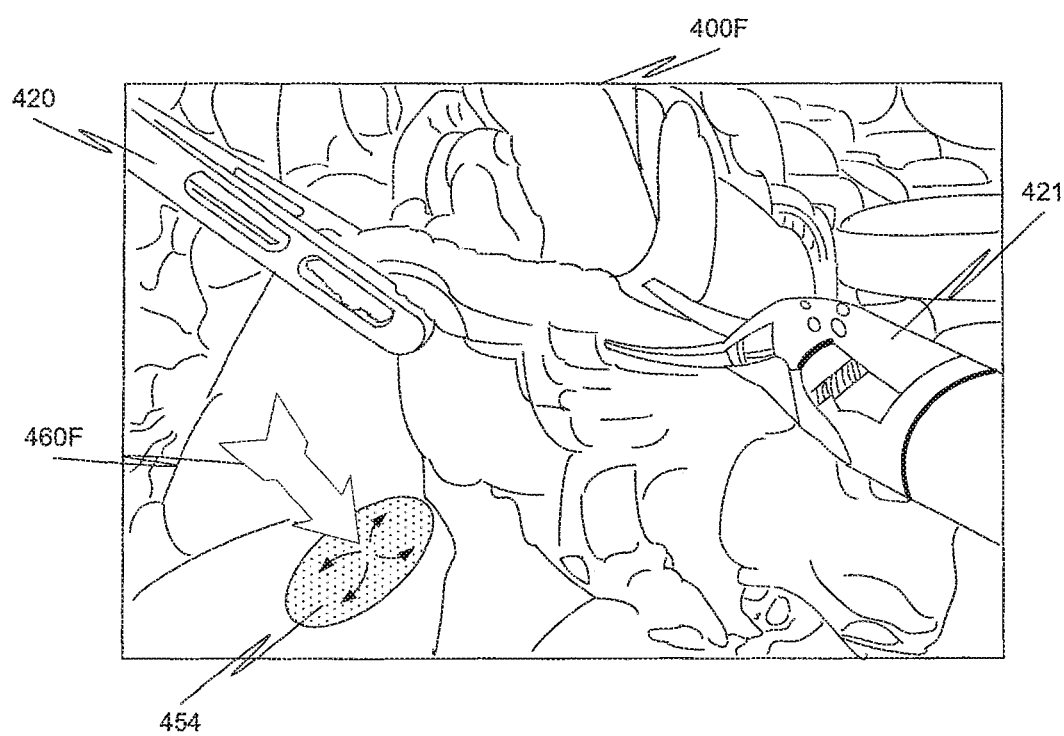

If the motion estimation flag still has the first state, MOTION DETECTION ENABLED check process 306 transfers to IDENTIFY REGION OF BLOOD process 307, which functions as described above, and so the region of blood is updated as illustrated in FIG. 4C. The bleeding has created a pool of blood 452 that obscures the original site 451 (FIG. 4B). Thus, if the surgeon missed scene 400B, pool of blood 452 provides only the information that bleeding is happening. However, initial site icon 460B is superimposed on scene 400C so that the surgeon has an indication of the site where bleeding was originally detected. This assists the surgeon in determining the location of the bleeding site.

To further assist the surgeon is locating the bleeding site, motion estimation may be or may have been enabled, e.g., the motion estimation flag is set to the second state. When the motion estimation flag has the second state, MOTION DETECTION ENABLED check process 306 (FIG. 3) transfers to BLOOD FLOW ESTIMATOR process 308.

In one aspect, BLOOD FLOW ESTIMATOR process 308 performs motion detection for the detected regions of blood instead of the whole scene and so saves time and makes the motion detection more robust. BLOOD FLOW ESTIMATOR process 308 generates a simulated blood flow in each region of blood. However, motion detection for regions of blood is illustrative only and is not intended to be limiting. In some aspects, motion detection for the whole scene can be used.

Also, in one aspect, BLOOD FLOW ESTIMATOR process 308 also includes the capability to determine the location of the first site icon using the information in REGION OF BLOOD AT (t−1) and the ability to access the information in INITIAL SITE 325. BLOOD FLOW ESTIMATOR process 308 uses motion to localize the position of the bleeding site.

In one aspect, using the information for locations in REGION OF BLOOD AT TIME t data 315 and the information for locations in REGION OF BLOOD AT TIME (t−1) data 320, the motion at each location is estimated. This estimation gives the gross motion at location (I, j) from time (t−1) to time t. The gross motion includes any tissue motion due to, for example, breathing or suctioning. In one aspect, the actual region used in the motion estimate is slightly larger than the region made up of locations marked as indicative blood. The size of the actual region is selected so that the motion estimation for the locations indicative of blood can be made reliably, in particular along the boundary. In addition, motion estimated slightly outside the region of blood can be used to help estimate blood flow, as described more completely below.

To localize the bleeding site for a region of blood, statistics of the motion in the region are used in one aspect of BLOOD FLOW ESTIMATOR process 308. The motion for a region is estimated by grouping and averaging the motion for all the locations in the region to generate an average motion of the region. At each location, the average motion of the region is subtracted from the motion at the location to obtain the relative blood motion at that location. In one aspect, all the relative motion radiates from the source of the bleeding, i.e., from the localized bleeding site. Upon obtaining the blood motion, i.e., the simulated blood flow in the region, blood flow estimator process 308 transfers processing to COMBINE BLOOD FLOW AND SCENE process 310.

COMBINE BLOOD FLOW AND SCENE process 310 generates a scene that, in one aspect, includes the acquired pixel data combined with an indicator of each region of blood, motion indicators of the blood flow, e.g., arrows that point in the direction of the flow, and the initial site icon. In one aspect, the motion indicators show only the relative flow of the blood. In another aspect, average tissue motion is indicated with a first color and first style of an indicator, and the relative flow of blood is indicated with a second color and second style of an indicator. The generated scene is sent to the display unit. In addition, the marking of each region of blood is optional in some aspects.

COMBINE BLOOD FLOW AND SCENE process 310 transfers to UPDATE REGION process 309. UPDATE REGION process 309 performs the same process as described above to save REGION OF BLOOD AT TIME t data 315 as REGION OF BLOOD AT TIME (t−1) data 320. UPDATE REGION process 309 returns to MONITOR FOR BLOOD process 301.

The linear progression in process 300 is illustrative only and is not intended to be limiting. The processes described can be performed in different sequences and/or in parallel so long as a process is not performed before the information needed by that process is available.

The examples described with respect to process 300 above are illustrative only and are not intended to be limiting. In some situations, both regions of blood and regions with blood motion may be displayed. For example, the static regions of blood could be displayed in a first color, and the regions of blood motion in a second different color. Alternatively, any region of blood could be displayed in a false color, e.g., green, and then arrows superimposed on the false coloring in regions of blood motion. The arrows represent the motion of the blood in that region. In this case, the false coloring, the arrows, or both could be switched on and off in the display by the surgeon. A localized bleeding site could be indicated by a flashing point in the display.

In one aspect, the initial site at which blood was detected is indicated by an initial site icon in each region of blood. The examples presented here are illustrative only and are not intended to be limiting to the specific embodiments described.

In addition, process 300 can be used for multiple different sites of bleeding. When multiple bleeding sites are detected, each site is monitored and tracked separately as described herein. If bleeding sites are all within a predefined distance, the sites can be combined and processed as a single site. The predefined distance is determined, for example, by the position resolution of process 300.

In one aspect, process 300 is performed on a sequence of frames so that the viewer sees a video stream. If the motion indicators change from frame to frame, the motion indicators appear, to the viewer, to be moving.

In another aspect, process 300 is used in combination with interactive process 350 (FIG. 3B). In process 350, a person is observing a display on a display unit in an operating room. The display unit could be stereoscopic display unit 251 in surgeon's console 250, an assistant's display unit, or some other display unit in the operating room. While other surgical actions may be in process, a warning of bleeding is generated on the display unit. In FIG. 4B, the warning of the region of blood is initial site icon 460B. When initial site icon 460B is detected by someone in the operating theater, BLEEDING INDICATOR check process 351 is complete, action continues in SUCTION process 352.

BLEEDING INDICATOR check process 351 should not be interpreted as requiring constant polling. Check process 351 means that no action with respect to locating an unknown source of bleeding is taken until an event occurs that warns of bleeding.

In SUCTION process 352, a physical region corresponding to region of blood 451 in the displayed scene is suctioned by manipulation of a surgical instrument by a person in the operating theater, e.g., either a surgeon or a surgeon's assistant. Scene 400D (FIG. 4D) is presented on the display unit at the conclusion of SUCTION process 352. Note that the person viewing the display, the viewer, sees a stereoscopic video sequence and scene 400D shows that at some point, it was possible to suction away enough blood that process 300 did not detect blood.

When process 300 does not detect blood in a scene, REGION check process 305 sets the initial site flag to true. Alternatively, or in addition, a system in minimally invasive surgical system 100 may detect suctioning and/or irrigation and set the initial site flag to true. Also, a user of minimally invasive surgical system 100 could set the initial site flag to a particular state via a user interface of surgical system 100.

SUCTION process 352 serves two purposes. Process 352 takes away blood so that the surgeon can see the surgical site. Process 352 can also take away blood that has pooled on the surface so that the bleeding site underneath the pool is exposed and the source of blood may be easier to locate. This allows viewing the blood as the amount of blood increases.

Next, in OBSERVE BLOOD FLOW process 353, one or more persons in the operating theater observe a scene on the display unit generated by method 300. The displayed scene includes the acquired scene of the surgical site combined with motion indicators of the true blood motion and at least one initial site icon. Scene 400E (FIG. 4E) is an example of a scene with motion indicators 453 and an initial site icon 460E. In one aspect, initial site icon 460E is turned off when motion indicators 453 are displayed. In this example, motion indicators 453 appear to radiate from a location near the center of the region of blood that is also pointed to by initial site icon 460E. By observing scene 400E, the viewer determines a location of the localized bleeding site.

If a location of the bleeding site is identified by the viewer using the information presented in the scene, the action in the operating theater transfers to REPAIR process 355 and otherwise returns to SUCTION process 352. In REPAIR process 355, the viewer or another person manipulates another surgical instrument to repair the bleeding site and so attenuate the bleeding.

Upon completion of REPAIR process 355, the display is observed to determine whether the repair was successful. In scene 400F (FIG. 4F), the repair of one bleeding site was successful, but scene 400F shows that there is a second region of blood that was masked by blood from the repaired site. Thus, in process 350, action can either return to SUCTION process 352 or return to REPAIR process 355 depending on whether scene 400F provides enough information to determine the location of the bleeding. In this example, scene 400F has the region of blood highlighted, e.g., false colored, and includes motion indicators 454 and initial site icon 460F. Note that bleeding detection module 136 continues to run throughout process 350 and so can detect additional blood and/or blood motion. The processes in method 350 are repeated until the repairs are successful and so the surgical procedure can continue. This is represented by SUCCESSFUL check process 357 in method 350.

Interactive process 350 is also used when multiple bleeding sites are detected. In this situation, when SUCTION process 352 is performed on one site, other sites that are far away are not re-initialized, because SUCTION process 352 does not affect these sites.

In a robotic surgical system, the position of the surgical instrument is known. The location of the bleeding site that is suctioned is also known. Using this distance information, and the location of the other bleeding sites, the process can determined which sites, if any, are outside the range of the suction instrument, and these sites are not re-initialized In one aspect, the scenes presented in FIGS. 4A to 4F are three-dimensional scenes. Thus, method 300 allows the surgeon to track the bleeding in three dimensions. Icons are overlain on the three-dimensional scenes in the three-dimensional real-time video to assist the surgeon in recognizing the presence of blood and in determining the localized bleeding site or sites. To generate the stereoscopic views with correct stereoscopic icons the processing described in U.S. Patent Publication No. US 2010/0166323 A1 (disclosing "Robust Sparse Image Matching for Robotic Surgery") is used to exclude the false detection scenario where a bleeding site is detected in only one of the two views used in the stereoscopic imaging.

While the bleeding detection process itself does not need positions of surgical instruments or tool tracking capability, the positions of surgical instruments and a tool tracking capability are provided by the robotic surgical system and can be used to augment the bleeding detection process. For example, the initial site icon can be properly positioned in the scene when the surgeon moves endoscope using the information provided by the robotic surgical system concerning the motion and location of the endoscope.

Figure 5:
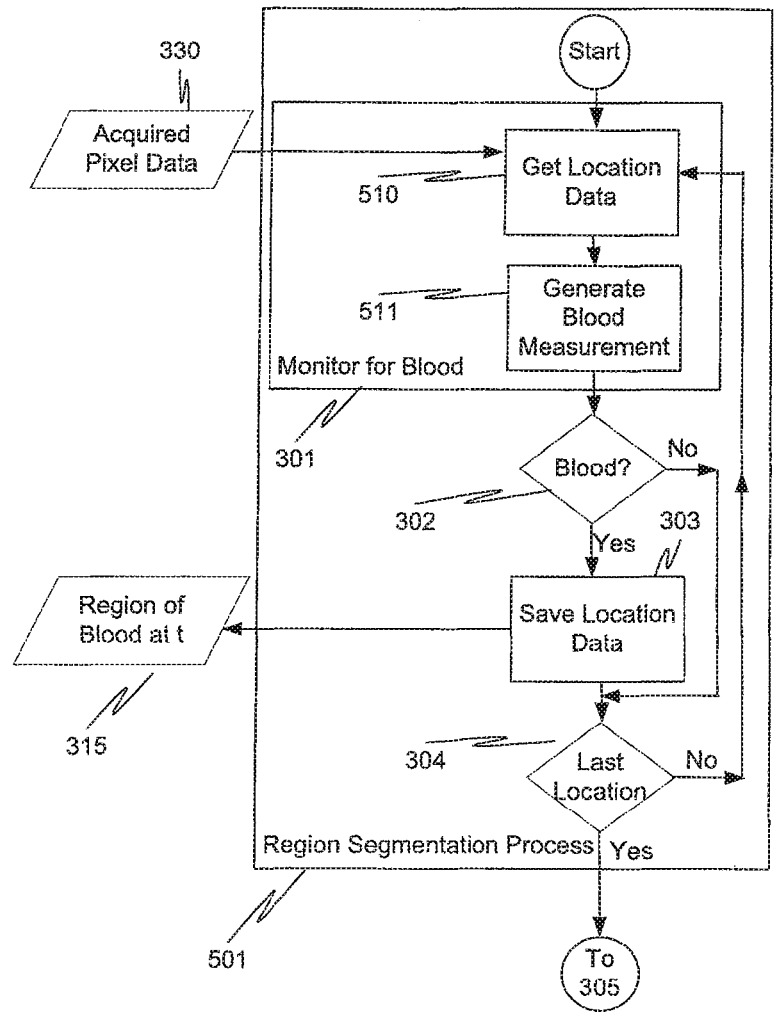
FIG. 5 is a more detailed process flow diagram of processes performed by a region segmentation module.

In one aspect, processes 301 to 304 are included in a region segmentation process 501 (FIG. 5). In this aspect, MONITOR FOR BLOOD process 301 (FIG. 3A) includes a GET LOCATION DATA process 510 and a GENERATE BLOOD MEASUREMENT process 511

For a location (i, j), GET LOCATION DATA process 510 retrieves a first block, sometimes called a window, of pixels of a first color component and a second block of pixels of a second color component. The first and second color components are different color components, e.g., the first color component is a red component, and the second color component is a green component.

Both the first block and the second block include location (i, j). For example, each block of pixels is a five pixel by five pixel block with location (i, j) at the center of the block. Herein, i ranges from 0 to the number of locations in the horizontal direction minus one, and j ranges from 0 to the number of locations in the vertical direction minus one.

It is not necessary that GET LOCATION DATA process 510 actually move any data. Process 510 provides information to GENERATE BLOOD MEASUREMENT process 511 on two sets of pixels that each include location (i, j). Each set of pixels is for a different color component. In the above example, each set of pixels was referred to as a block of pixels.

GENERATE BLOOD MEASUREMENT process 511 processes the first block of pixels to generate a filtered value R for the pixel of the first color component at location (i, j). GENERATE BLOOD MEASUREMENT process 511 processes the second block of pixels to generate a filtered value G for the pixel of the second color component at location (i, j). In one aspect, a five by five Gaussian filter is used to generate filtered value R and to generate filtered value G.

In this aspect to generate the blood measurement BM(I, j), GENERATE BLOOD MEASUREMENT process 511 generates a ratio (R/G). In another aspect to generate the blood measurement BM(i, j), GENERATE BLOOD MEASUREMENT process 511 generates a ratio ((R+0.5)/(G+0.5)). In one aspect, filtered value R and filtered value G range from zero to 255. In either aspect, blood measurement BM(i, j) is set equal to the value of the ratio. In general terms, GENERATE BLOOD MEASUREMENT process 511 generates a ratio in which a first quantity in the ratio include a value determined using a first color component pixel value at location (i, j) and in which a second quantity in the ratio includes a value determined using a second color component value at location (i, j).

It has been empirically determined that when blood measurement BM(i, j) has a value larger than a blood indication threshold, there is a very high probability that blood is present at location (i, j). Conversely, when blood measurement BM(i, j) has a value smaller than the blood indication threshold, there is not blood at location (i, j). Thus, BLOOD check process 302, in this aspect, compares blood measurement BM(I, j) to the blood indication threshold to determine whether blood measurement BM(i, j) is indicative of blood at location (i, j). To be conservative, a blood indication threshold is chosen that minimizes the chance of missing the detection of blood.

In one aspect, for a surgical scene and a color model that includes a red color component and a green color component, GENERATE BLOOD MEASUREMENT process 511 generates the ratio (R/G) as blood measurement BM(i, j). For this aspect, a blood indication threshold of three was used. Also, in this aspect, the range of values of the red color component and of the green color component was from zero to 255.

The other processes in REGION SEGMENTATION process 501 are the same as described with respect to processes with the same reference numeral in FIG. 3A. Thus, the description of those processes is not repeated.

Figure 6:
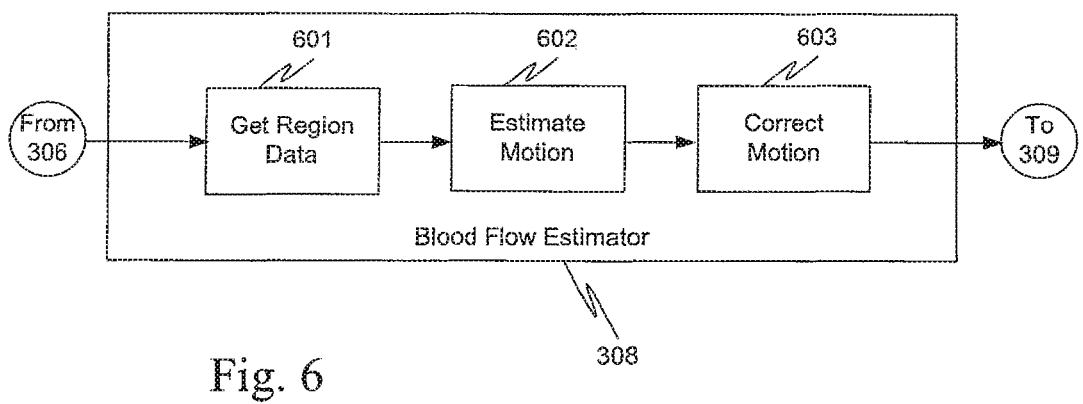
FIG. 6 is a more detailed process flow diagram of the blood flow estimator process of FIG. 3A.

FIG. 6 is a more detailed process flow diagram of one aspect of BLOOD FLOW ESTIMATOR process 308. GET REGION DATA process 601 accesses the pixel data for a region of blood at times t and (t−1) and transfers processing to ESTIMATE MOTION process 602.

In one aspect, ESTIMATE MOTION process 602 implements an optical flow model that utilizes hierarchical motion estimation to generate the motion of the region from time (t−1) to time t. The motion estimation framework includes (i) pyramid construction, (ii) motion estimation, (iii) image warping, and (iv) coarse-to-fine refinement. The optical flow model works best for scenes that have color consistency from frame to frame and brightness consistency from frame to frame.

The use of the optical flow model to estimate motion of a region is known and so is not considered in further detail. See for example, J. R. Bergen, P. Anandan, K. J. Hanna, and R. Hingorani, "Hierarchical Model-Based Motion Estimation," European Conference on Computer Vision, pages 237-252, (1992), which is incorporated herein by reference. In one aspect, ESTIMATE MOTION process 602 provides the motion at time t for each location (i, j) in the region by using a window that is, for example, five locations by five locations centered about that location.

The motion provided by ESTIMATE MOTION process 602 is the gross motion of the region that includes any motion of tissue and any motion of the blood. CORRECT MOTION process 603 receives the gross motion from process 602 and removes the motion of the tissue to obtain the blood motion. As indicated above, in one aspect, a statistical evaluation is used to remove the motion of the tissue. The motion at location (i, j) is defined as:

$$M(i,j) = M_{Tissue}(i,j) + M_{Blood}(i,j)$$

where

M(i, j) is gross motion at location (i, j) from process 602,
$M_{Tissue}$(i, j) is tissue motion at location (i, j), and
$M_{Blood}$(i, j) is blood motion at location (I, j).

Tissue motion $M_{Tissue}$(i, j) at location (i, j) is estimated as the average motion over the region. Similarly, blood flow $M_{Blood}$(i, j) is estimated as the average motion over the region.

$$M_{Tissue\_avg} = (1/n) * \sum_{Windows} M_{Tissue}(i,j)$$

$$M_{Blood\_avg} = (1/n) * \sum_{Windows} M_{Blood}(i,j)$$

$$M_{avg} = (1/n) * \sum_{Windows} M_{Tissue}(i,j) + (1/n) * \sum_{Windows} M_{Blood}(i,j)$$

where n is the number of locations in the region.

However, centered around a radiating bleeding source, the motion of the blood is assumed equal in all directions and so the average motion of the blood is zero. With this assumption, the average motion at location (i, j) is just the average motion of the tissue. Thus, the motion of the blood at location (i, j) is:

$$M_{Blood}(i,j) = M(i,j) - M_{avg}$$

While this correction process does not include gravity effects and assumes isotropic blood flow, the process provides sufficient detail to assist the surgeon in locating the bleeding site. Complete accuracy is not needed to assistance the surgeon in confirming bleeding sites and localizing bleeding sources.

In general, if the purpose is not simply localizing the bleeding site, the motion correction process can assume that the averaged tissue motion can be determined from a bordering area just outside the region of blood. With this assumption, the blood flow can be obtained by subtracting the averaged tissue motion from the gross motion.

Figure 7:
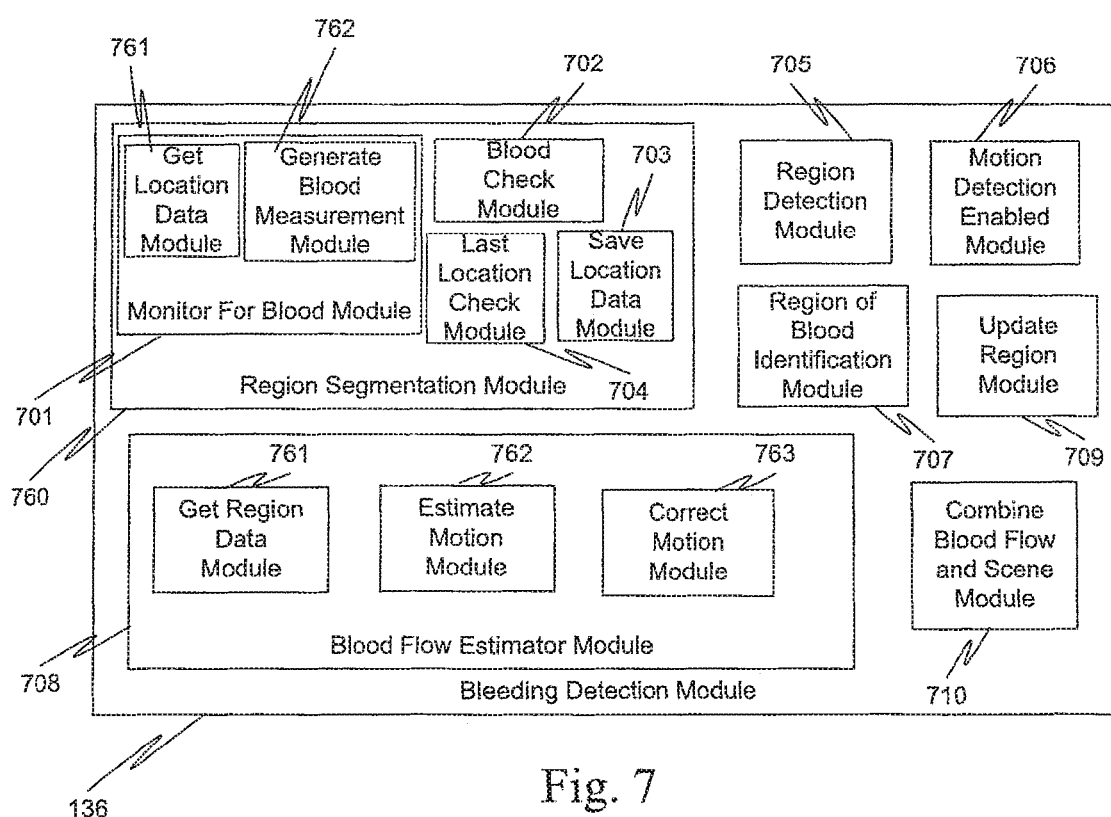
FIG. 7 is a more detailed diagram of modules included in the bleeding detection module of FIG. 1.

FIG. 7 is a more detailed diagram of one aspect of bleeding detection module 136. Bleeding detection module 136 includes a region segmentation module 760 that in turn includes a monitor for blood module 701, a blood check module 702, a save location data module 703, and a last location check module 704.

Monitor for blood module 701 includes a get location data module 761 and a generate blood measurement module 762. Monitor for blood module 701 performs MONITOR FOR BLOOD process 301 (FIG. 3A). Get location data module 761 (FIG. 7) performs GET LOCATION DATA process 510 (FIG. 5), while generate blood measurement module 762 performs GENERATE BLOOD MEASUREMENT process 511. Blood check module 702, save location data module 703, and last location check module 704 perform BLOOD check process 302, SAVE LOCATION DATA process 303, and LAST LOCATION check process 304, respectively.

Bleeding detection module 136 also includes a region detection module 705, a motion detection enabled module 706, a region of blood identification module 707, and an update region module 709. Region detection module 705 performs REGION check process 305. Motion detection enabled module 706 and region of blood identification module 707 perform MOTION DETECTION ENABLED check process 306 and IDENTIFY REGION OF BLOOD process 307, respectively. Update region module 709 performs UPDATE REGION process 309.

Bleeding detection module 136 also includes a blood flow estimator module 708, and a combine blood flow and scene module 710. Blood flow estimator module 708 performs BLOOD FLOW ESTIMATOR process 308. Combine blood flow and scene module 710 performs COMBINE BLOOD FLOW AND SCENE process 310.

Blood flow estimator module 708 includes a get region data module 761, an estimate motion module 762, and a correct motion module 763. Get region data module 761, estimate motion module 762, and correct motion module 763 perform GET REGION DATA process 601, ESTIMATE MOTION process 602, and CORRECT MOTION process 603, respectively.

As noted above, each of the modules in FIG. 7 can be implemented by computer program instructions executing on a processor, firmware, hardware, or any combination of the three. When computer program instructions are used, the instructions are stored on a memory and executed on the processor. Thus, when it is said that a module performs an action and the module includes computer instructions, those knowledgeable in the field understand that it means the computer instructions are executed on the processor.

The modules presented in FIG. 7 are illustrative only and are not intended to be limiting to the specific set of modules illustrated. For example, if the modules are implemented using computer instructions, all the modules may be part of a single computer program and execution of one or more instructions in that program perform the function of a module.

In the above aspects, bleeding detection unit 135 is used to determine whether there are one or more regions of blood in a scene of a surgical site and to determine the relative motion of the blood in each of the one or more regions. This automatic detection provides a new capability to a surgeon by allowing the surgeon to respond promptly to any new source of blood.

However, there is always blood present during surgery and in some aspects, the operation of bleeding detection unit 135 is based on one or more factors such as the state of various components in a minimally invasive surgical system, the field of view of the surgeon, and perhaps the preferences of the surgeon. This permits the information provided by bleeding detection unit 135 to be more relevant by not overloading the surgeon with useless information. For example, when the surgeon focuses on a region to cut and begins an incision, a warning of bleeding in that region would not be of particular use to the surgeon. The surgeon is focusing on the region and bleeding is expected. However, detection of bleeding in an area outside the region being focused on, i.e., outside the fovea or the middle of the field of view, would be of use to the surgeon.

In one aspect, the presentation of regions for which blood is detected by bleeding detection unit 135 is controllable as is the presentation of regions for which blood flow estimation is performed. For example, an area of the surgical scene is specified in which blood detection is not desired. If a region of blood falls within this area, the region of blood is not identified in the displayed scene. Conversely, if the region of blood is outside the area, the region of blood is identified in the displayed scene. Such areas can be determined based on user input, or automatically based on inputs from the surgical system, or a combination of the two.

Figure 8A:
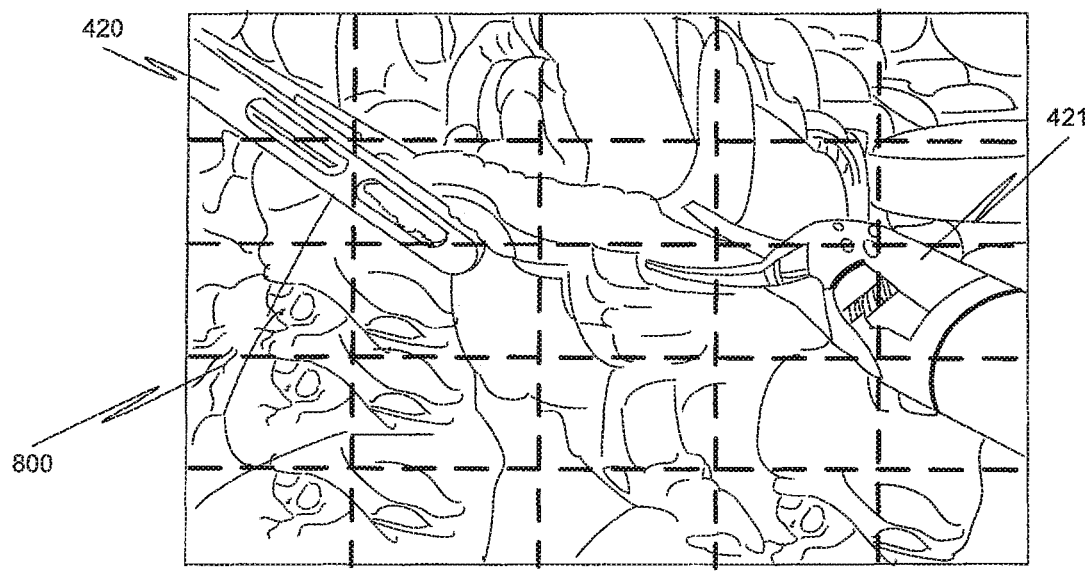
FIG. 8A is an example of a grid superimposed on a scene to permit a user to specify areas for bleeding detection.

In one aspect, a user activates a bleeding detection mode select input interface 253 in a user interface 262. In response, the user is presented with options to control the bleeding detection process. For example, as illustrated in FIG. 8A, a grid 800 is superimposed on the displayed scene of the surgical site, and the user selects the areas in which bleeding detection is desired. This allows the user to specify the areas in which bleeding detection is of particular concern as well as the areas in which bleeding detection is not of concern. Note that the use of grid 800 to specify the different areas is illustrative only and is not intended to be limiting.

Also, bleeding detection could be turned on for the whole scene by default and the surgeon could use bleeding detection mode select input interface 253 to indicate areas for which bleeding detection is turned off completely or in part at any time during the procedure. Turning bleeding detection off in part means, for example, that blood flow estimator 308 is turned off, but the detection and indication of blood continues to function normally. Also, blood flow estimator 308 may continue to run in the background, but the output of blood flow estimator 308 is not used when bleeding detection is turned off in part.

Figure 8B:
FIG. 8B is an example of an area selected by the surgical system in which bleeding detection is turned off.

In another aspect, surgical system 100 automatically determines an area or areas in the surgical scene that are not monitored for blood. For example, when endoscope 112 is moving only the amount necessary to maintain focus and the surgical instruments or instruments in use are known to cause bleeding, bleeding detection is limited by surgical system 100 to the area outside the fovea of the surgeon, e.g., outside the middle field of view indicated by circle 803 in FIG. 8B. Of course, a combination of user input and system inputs can be used to specify the areas for blood detection and/or blood flow estimation.

Figure 9:
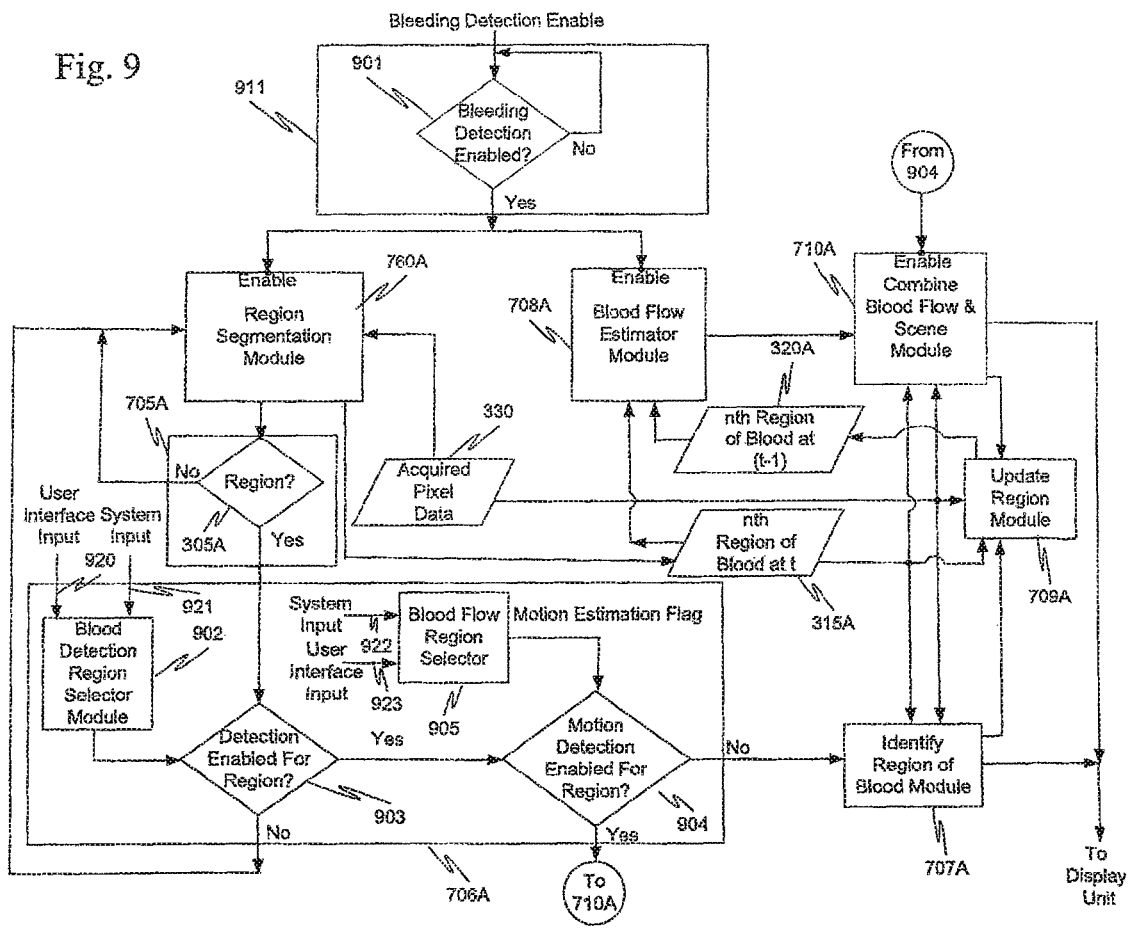
FIG. 9 is a schematic of a bleeding detection system with controls for blood detection and blood flow estimation.

FIG. 9 is a process flow diagram of a method 900 that permits control over bleeding detection module 135. In the aspect of FIG. 9, the operation of region segmentation module 760A and blood flow estimator module 708A is controlled by bleeding detection-enabled module 911. A bleeding detection enable signal is provided to module 911.

In one aspect, the state of the bleeding detection enable signal is determined by an input from bleeding detection mode select 253 via user interface 262. Alternatively, the state of the bleeding detection enable signal is determined by an input or inputs from the control system of the surgical system. When the bleeding detection enable signal has a first state, BLEEDING DETECTION ENABLED check process 901 does not pass an enable signal to region segmentation module 760A and blood flow estimator module 708A. However, when the bleeding detection enable signal has a second state, BLEEDING DETECTION ENABLED check process 901 enables segmentation module 760A and blood flow estimator module 708A. Thus, in this aspect, enabled segmentation module 760A and blood flow estimator module 708A are always running.

In FIG. 9, modules 760A, 705A, 707A, 708A, 709A, and 710A are equivalent to modules 760, 705, 707, 708, 709, and 710, respectively, and so the processes performed by these modules are equivalent to those described above. Thus, the processes are not repeated here.

In this aspect, motion detection enabled module 706 is replaced by module 706A that permits control of both the regions for which blood is identified in the display, and the regions for which blood flow estimation is displayed. When processing transfers to module 706A at least one region of blood has been detected in an acquired scene of the surgical site. Module 706A first determines whether blood detection is enabled for each region of blood that has been detected.

Specifically, for each region of blood found by region segmentation module 760A, DETECTION ENABLED FOR REGION check process 903 determines whether the input received from blood detection region selector module 902 permits blood detection for that region. In this aspect, blood detection region selector module 902 receives both user input 920 and system input 921.

As described above, user input 920 specifies areas in the scene for which blood detection is desired and other areas for which blood detection is not desired. System input 921 is signals from systems within the surgical system that identify the state of the surgical system, e.g., the velocity of endoscope 112, the surgical instrument or instruments that is currently being controlled by the surgeon, and data characterizing the motion of each of the controlled surgical instruments. Blood detection region selector module 902 analyses the input information and sends a signal or signals to DETECTION ENABLED FOR REGION check process 903 to indicate the area(s) in the acquired surgical scene for which blood detection is desired.

For example, if the user input indicates that blood detection is not desired in an area, but the data on endoscope 112 indicates that endoscope 112 is moving such that the cameras cannot focus, module 902 enables blood detection for the entire scene until the camera comes into focus and then reverts to the user selections. Since the procedure is in transition as indicated by the movement of endoscope 112, blood detection is enabled so that any blood is detected at the earliest possible time. Conversely, if endoscope 112 is not moving rapidly, and a surgical instrument is being used that results in bleeding, blood detection is turned off for the areas indicated by the user input. In addition, system input 921 may turn off blood detection for the area in the fovea of the surgeon. Thus, based on inputs 920, 921, module 902 provides information to check process 903 that identifies a specific area or areas that are not enabled for blood detection. Conversely, module 902 could provide information to check process 903 that identifies areas that are enabled for blood detection.

Thus, for each region of blood from region segmentation module 760A, DETECTION ENABLED FOR REGION check process 903 compares the region to the areas specified by module 902 for which blood detection is not enabled. For each region of blood, check process 903 indicates whether blood detection is enabled for the region. If blood detection is not enabled for any of region of blood, check process 903 returns to region segmentation module 760A. If blood detection is enabled for one or more regions of blood, check process 903 passes those regions to MOTION DETECTION ENABLED FOR REGION check process 904. When it is said that a region is passed, it should not be interpreted that the region is physically passed. Rather, an indicator or indicators are provided that indicates whether blood detection is enabled for that region, e.g., a blood detection enabled bit is set to true for the region.

Similar to the above description, the state of a motion estimation flag determines the action determined by MOTION DETECTION ENABLED FOR REGION check process 904. In this aspect, blood flow region selector module 905 determines the state of motion estimation flag for each region that has blood detection enabled. In this aspect, blood flow region selector module 905 receives both user input 923 and system input 922.

For example, the user could indicate via bleeding detection module select input interface 253 that for some areas blood detection was desired, but blood flow estimation was unnecessary. The state information provided as system input 922 could indicate that the surgical procedure is just starting and so blood flow region selector module 905 turns off blood flow estimation for all regions irrespective of the user input. Module 905 could turn on blood flow estimation when a surgical instrument that can cause bleeding is first activated so that any bleeding can be detected as quickly as possible.

For each region of blood from region segmentation module 760A for which bleeding detection is enabled, MOTION DETECTION ENABLED FOR REGION check process 904 uses the state of the motion estimation flag for the region to determine whether to pass the region to identify region of blood module 707A or to pass the region to combine blood flow and scene module 710A. Thus, blood flow could be estimated for some regions of blood and not for other regions of blood in the same acquired scene. In this case, the operation of modules 707A and 710A is coordinated to create the displayed scene.

The examples used with respect to FIG. 9 are illustrative only and are not intended to be limiting. In this example, the segmentation and blood flow estimation were enabled and then allowed to run continuously and the output to the display unit was controlled. Alternatively, the segmentation and blood flow estimation could be started at start-up, and the acquired pixel data provided only when it was desired to have the bleeding detection capability. Similarly, the control of bleeding detection and blood region segmentation and blood flow estimation processes can be configured based on surgeon preference, the surgical procedure being performed, or a combination of the two. In one aspect, the segmentation and blood flow estimation are continuously running in the background, even when they have been turned off via a user interface, so that immediate information is available when segmentation and/or blood flow estimation are turned on via the user interface.

As used herein, "first," "second," and "third" are adjectives used to distinguish between different components. Thus, "first," "second," and "third" are not intended to imply any ordering of the components.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Memory refers to a volatile memory, a non-volatile memory, or any combination of the two. A processor is coupled to a memory containing instructions executed by the processor. This could be accomplished within a computer system, or alternatively via a connection to another computer via modems and analog lines, or digital interfaces and a digital carrier line.

Herein, a computer program product comprises a non-transitory medium configured to store computer readable code needed for any one or any combination of the operations described with respect to the bleeding detection system or in which computer readable code for any one or any combination of operations described with respect to the bleeding detection system is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a non-transitory tangible medium configured to store computer readable instructions for any one of, or any combination of operations described with respect to the bleeding detection system or in which computer readable instructions for any one of, or any combination of operations described with respect to the bleeding detection system are stored. Non-transitory tangible computer program products are CD-ROM discs, DVD discs, flash memory, ROM cards, floppy discs, magnetic tapes, computer hard drives and other non-transitory physical storage mediums.

We claim:

1. A system for blood detection in a surgical site scene comprising:
   a bleeding detection unit configured to be connected between an image capture system and a display unit;
   the bleeding detection unit being configured to receive a frame of data of a scene of a surgical site from the image capture system during a surgical procedure, the frame of data includes a plurality of locations, and each location of the plurality of locations includes a color pixel, and the color pixel includes a plurality of color component pixels, the bleeding detection unit including:
      a region segmentation module configured to:
         receive the frame of data;
         detect whether the plurality of color component pixels of each location includes information indicative of blood at that location; and
         determine a region of blood in the scene based on locations detected as including information indicative of blood;
      a region of blood identification module coupled to the region segmentation module, and configured to:
         generate an initial site icon, during the surgical procedure, to indicate an initial region of blood in the scene, when the region of blood in the scene is the initial region of blood in the scene, wherein the generate an initial site icon is performed after the determine a region of blood in the scene; and
         combine the initial site icon with the scene to generate data including a combined scene; and
      the bleeding detection unit being configured to output the data including the combined scene to the display unit.

2. The system of claim 1, wherein the bleeding detection unit further comprises:
   a blood flow estimator module, wherein the blood flow estimator module simulates flow of blood in the region of blood in the scene.

3. The system of claim 2, wherein the blood flow estimator module includes:
   an estimate motion module configured to estimate gross motion at each location in the region of blood in the scene.

4. The system of claim 3, the estimate motion module being configured to estimate the gross motion at each location in the region of blood in the scene based on an optical flow analysis using a plurality of frames of data of the scene of the surgical site.

5. The system of claim 3, wherein the blood flow estimator module includes:
   a correct motion module coupled to the estimate motion module, wherein the correct motion module corrects the gross motion at each location to estimate motion of blood at that location.

6. The system of claim 5, the correct motion module being configured to correct the estimated gross motion of the location to compensate for average tissue motion at the location.

7. The system of claim 1, wherein the initial site icon comprises an arrow.

8. The system of claim 1, the region of blood identification module further being configured to identify the region of blood in the scene with a blood marker, wherein the blood marker is different from the initial site icon.

9. The system of claim 1, wherein the region segmentation module configured to detect whether the plurality of color component pixels of each location includes information indicative of blood at that location further comprises:
   a generate blood measurement module configured to generate a ratio in which a first quantity in the ratio includes a value determined using a first color component pixel value at a location, and in which a second quantity in the ratio includes a value determined using a second color component pixel value at the location; and
   a blood check module configured to identify the location as including information indicative of blood if the ratio has a predefined relationship to a blood indication threshold.

10. The system of claim 9, wherein the predefined relationship is that the ratio is larger than the blood indication threshold.

11. A system comprising:
    a memory storing instructions; and
    a processor communicatively coupled to the memory and configured to execute the instructions to:
       receive, from an image capture system during a surgical procedure, a first frame of data of a scene of a surgical site;
       identify, during the surgical procedure and based on the first frame, an initial region of blood in the scene;
       receive, from the image capture system during the surgical procedure and subsequent to the receiving of the first frame, a second frame of data of the scene of the surgical site, the second frame of data including data representative of a region of blood that includes the initial region of blood in the scene;
       generate, during the surgical procedure and after the identifying of the initial region of blood in the scene, data representative of a combined image comprising the second frame and a visual indicator indicating the initial region of blood in the scene; and
       transmit, during the surgical procedure, the data representative of the combined image to a display unit for display of the combined image.

12. The system of claim 11, wherein the processor is further configured to execute the instructions to turn on and/or turn off display of the visual indicator in response to a predetermined user input.

13. The system of claim 11, wherein:
    the processor is further configured to execute the instructions to select a region of the frame to be excluded from blood detection processing, and
    the identifying of the initial region of blood in the scene is not based on the selected region of the frame.

14. The system of claim 13, wherein the selected region of the frame is selected based on at least one of user input and information received from a surgical system used to perform the surgical procedure.

15. The system of claim 11, wherein the combined image is a stereoscopic image and the visual indicator is a stereoscopic visual indicator.

16. A method comprising:
receiving, by a bleeding detection system from an image capture system during a surgical procedure, a first frame of data of a scene of a surgical site;
identifying, by the bleeding detection system during the surgical procedure and based on the first frame, an initial region of blood in the scene;
receiving, by the bleeding detection system from the image capture system during the surgical procedure and subsequent to the receiving of the first frame, a second frame of data of the scene of the surgical site, the second frame of data including data representative of a region of blood that includes the initial region of blood in the scene;
generating, by the bleeding detection system during the surgical procedure and after the identifying of the initial region of blood in the scene, data representative of a combined image comprising the second frame and a visual indicator indicating the initial region of blood in the scene; and
transmitting, by the bleeding detection system during the surgical procedure, the data representative of the combined image to a display unit for display of the combined image.

17. The method of claim 16, further comprising:
performing, by the bleeding detection system during the surgical procedure, at least one of turning on and turning off display of the visual indicator in response to a predetermined user input.

18. The method of claim 16, further comprising:
selecting, by the bleeding detection system during the surgical procedure, a region of the frame to be excluded from blood detection processing,
wherein the identifying of the initial region of blood in the scene is not based on the selected region of the frame.

19. The method of claim 18, wherein the region of the frame is selected based on at least one of user input and information received from a surgical system used to perform the surgical procedure.

20. The method of claim 16, wherein the combined image is a stereoscopic image and the visual indicator is a stereoscopic visual indicator.

* * * * *